US010584162B2

United States Patent
Kozel et al.

(10) Patent No.: US 10,584,162 B2
(45) Date of Patent: Mar. 10, 2020

(54) FUNGAL DETECTION USING MANNAN EPITOPE

(71) Applicant: BOARD OF REGENTS OF THE NEVADA SYSTEM OF HIGHER EDUCATION, ON BEHALF OF THE UNIVERSITY OF NEVADA, RENO, Reno, NV (US)

(72) Inventors: Thomas R. Kozel, Reno, NV (US); Breeana Hubbard, Pullman, WA (US); Amanda Burnham-Marusich, Reno, NV (US)

(73) Assignee: Board of Regents of the Nevada System of Higher Education, on behalf of the University of Nevada, Reno, Reno, NV (US)

( * ) Notice: Subject to any disclaimer, the term of this patent is extended or adjusted under 35 U.S.C. 154(b) by 0 days.

(21) Appl. No.: 15/567,547

(22) PCT Filed: Apr. 23, 2016

(86) PCT No.: PCT/US2016/029085
§ 371 (c)(1),
(2) Date: Oct. 18, 2017

(87) PCT Pub. No.: WO2016/172660
PCT Pub. Date: Oct. 27, 2016

(65) Prior Publication Data
US 2018/0148498 A1    May 31, 2018

Related U.S. Application Data

(60) Provisional application No. 62/151,865, filed on Apr. 23, 2015.

(51) Int. Cl.
| | | |
|---|---|---|
| A61K 39/395 | (2006.01) | |
| A61K 39/00 | (2006.01) | |
| C07H 21/02 | (2006.01) | |
| C07K 16/14 | (2006.01) | |
| C07K 16/44 | (2006.01) | |
| G01N 33/569 | (2006.01) | |

(52) U.S. Cl.
CPC ............ *C07K 16/14* (2013.01); *C07K 16/44* (2013.01); *G01N 33/56961* (2013.01); *C07K 2317/33* (2013.01); *C07K 2317/622* (2013.01); *C07K 2317/92* (2013.01)

(58) Field of Classification Search
CPC ...................... A61K 39/395; A61K 39/39575
USPC ......... 424/130.1, 135.1, 139.1, 141.1, 163.1, 424/164.1, 184.1, 274.1
See application file for complete search history.

(56) References Cited

U.S. PATENT DOCUMENTS

| | | |
|---|---|---|
| 5,665,539 A | 9/1997 | Sano et al. |
| 6,283,761 B1 | 9/2001 | Joao |
| 2005/0239108 A1 | 10/2005 | Barletta et al. |
| 2011/0189183 A1* | 8/2011 | Williamson ............ C07K 14/40 424/135.1 |

FOREIGN PATENT DOCUMENTS

WO   2014174293 A1   10/2014

OTHER PUBLICATIONS

Uniprot accession No. P39107; Feb. 1, 1995.
Azuma, et al., Chemical and Immunological Properties of Galactomannans Obtained from Histoplasma duboisii, Histoplasma capsulatum, Paracoccidioides brisiliensis and Blasomyces dermatitidis., Mycopathologicia et Mycologia applicata, vol. 54, 1, pp. 111-125, 1974.
Ballou, et al., *Saccharomyces cerevisiae* Mutants that make Mannoproteins with a Truncated Carbohydrate Outer Chain., 1980, J Bio Chem 255(12):5986-5991.
Elad, et al., Feed contamination with Candida krusei as a probable source of mycotic mastitis in dairy cows., J Am Vet Med Assoc Sep. 1, 1995; 207(5):620-2—Abstract.
Gopal, et al., Regulation of the protein glycosylation pathway in yeast: Structural control of N-linked oligosaccharide elongation., Proc Natl Acad Sci USA vol. 84, pp. 8824-8828, Dec. 1987.
Herscovics, et al., Glycoprotein biosynthesis in yeast., 1993, FASEB J 7:540-550.
Jungmann, et al., Multi-protein complexes in the cis Golgi of *Saccharomyces cerevisiae* with α-1,6-mannosyltransferase activity., The EMBO Journal vol. 17 No. 2 pp. 423-434, 1998.
Jungmann, et al., The *Saccharomyces cerevisiae* Protein Mnn10p/Bed1p Is a Subunit of a Golgi Mannosyltransferase Complex, 1999, J Biol Chem 274(10):6579-6585.
Kobayashi, et al., Structural Study of Phosphomannan of Yeast-Form Cells of Candida albicans J-1012 Strain with Special Reference to Application of Mild Acetolysis., 1989, Archives of Biochemistry and Biophysics 272(2):364-375.
Latge, et al., Chemical and Immunological Characterization of the Extracellular Galactomannan of Aspergillus fumigatus., 1994, Infection and Immunity 62(12):5424-5433.
Miyazaki, et al., Immunochemical Examination of the Polysaccharides of Mucorales., (1980) In Sandford PA, Matsuda K (ed), Fungal polysaccharides, Symposium Series No. 126.
Nelson, et al., Demystified . . . Monoclonial antibodies., 2000, J Clin Pathol: Mol Pathol 53:111-117.

(Continued)

*Primary Examiner* — Rodney P Swartz
(74) *Attorney, Agent, or Firm* — Saul Ewing Arnstein & Lehr LLP; Kathryn Doyle

(57) ABSTRACT

Non-invasive methods are provided herein for diagnosing samples as including a fungus, including fungal infection or contamination, with specific monoclonal antibodies capable of detecting molecules associated with fungi in the sample, such as a biological or environmental sample. These molecules can be identified using various methods, including but not limited to antibody based methods, such as an enzyme-linked immunosorbant assay (ELISA), or a lateral flow immunoassay.

10 Claims, 8 Drawing Sheets

Specification includes a Sequence Listing.

(56) References Cited

OTHER PUBLICATIONS

Peat, et al., Polysaccharides of Baker's Yeast. Part IV. Mannan, (1961) J Chem Soc 1:29-34.

Reiss, et al., Galactomannan Antigenemia in Invasive Aspergillosis., (1979) Infect Immun 25:357-365.

Sano, et al., Immuno-PCR: very sensitive antigen detection by means of specific antibody-DNA conjugates, Science. 258.5079 (Oct. 2, 1992): p. 120+. (5 pages).

Schile, et al., Abstract B10: Diversity Outbred: A new, highly diverse mousetock for toxicology and cancer., Abstract B10, AACR-NCI-EORTC International Conference: Molecular Targets and Cancer Therapeutics—Nov. 12-16, 2011, San Francisco, CA.

Strahl-Bolsinger, et al., Protein O-mannosylation., Biochima et Biophysica Acta 1426 (1999) 297-307.

Weiner, et al., Mannan Antigenemia in the Diagnosis of Invasive Candida Infections., (1976) J Clin Invest 58:1045-1053.

Wheat, et al., Diagnosis of Disseminated Histoplasmosis by Detection of Histoplasma capsulatum Antigen in Serum and Urine Specimens., N Engl J Med 1986; 314:83-88.

European Patent Application No. 16784054.6—Extended European Search Report dated Aug. 21, 2018.

Ataoglu, et al.,"Characterization of Epitopes Recognized by Candida Factor 1 and 9 Antisera by Use of *Saccharomyces cerevisiae* mnn Mutants," 1993, Infection and Immunity 61(8):3313-3317.

Burnham-Marusich, et al.,"Conservation of Mannan Synthesis in Fungi of the Zygomycota and Ascomycota Reveals a Broad Diagnostic Target," 2018, mSphere 3(3):e00094-18 (pp. 1-14).

Hall, et al.,"Mannosylation in Candida albicans: role in cell wall function and immune recognition.", 2013, Molecular Microbiology 90(6):1147-1161.

Ikuta, et al.,"NMR assignment of the galactomannan of Candida lipolytica," 1997, FEBS Letters 414(2):338-342.

Schwientek, et al.,"Golgi Localization and in Vivo Activity of a Mammalian Glycosyltransferase (Human beta-1, 4-Galactosyltransferase) in Yeast.", 1996, The Journal of Biologic Chemistry 271(7):3398-3405 (Issue of Feb. 15).

Zhang, et al.,"Human Recombinant Antimannan Immunoglobulin G1 Antibody Confers Resistance to Hematogenously Disseminated Candidiasis in Mice.", 2006, Infection and Immunity 74(1):362-369.

Zhong, et al.,"High-temperature cultivation of recombinant Pichia pastoris increases endoplasmic reticulum stress and decreases production of human interleukin-10", 2014, Microbial Cell Factories 13(1):163 (10 pages).

\* cited by examiner mAb 2DA6 DNA Sequence
Light chain: DNA sequence (384 bp) (SEQ ID NO: 1)

```
|                            Leader sequence                          |
  ATGGATTTTCAGGTGCAGATTTTCAGCTTCCTGCTAATCAGTGCCTCAGTCATTATGTCCAGAGGA C

FR1
AAATTGTTCTCACCCAGTCTCCAGCAATCATGTCTGCATCTCCAGGGCAGAAAGTCACCATAACCTG

|            CDR1                  |                  FR2
C AGTGTCAGCTCAAACATACATTTCATGCAC TGGTACCAGCAGAAGTTAGGATTCTCCCCCAAACTC

|      CDR2        |
TGGATTTAT GACACATCCAAACTGACTCCT GGAGTCCCTGCTCGCTTCAGTGGCAGTGGGTCTGGGA

FR3                                                   |
CCTCTTACTCTCTCACAATCAGCAGCATGGAGGCTGAAGATGCTGCCTCTTATTTCTGC CATCAGTG

CDR3              |         FR4             |
GAGTAGTCACCCACATACG TTCGGATCGGGGACCAAGCTGGAAATAAAA
```

Heavy chain: DNA sequence (408 bp) (SEQ ID NO: 2)

```
|                            Leader sequence                          |
  ATGGATTGGACCTGGGTCTTTCTCTTCCTCCTGTCAGTAACTGCAGGTGTCCACTCC CAGGTTCAGC

FR1
TGCAGCAGTCTGGAGCTGAGCTGATGAAGCCTGGGGCCTCAGTGAGGCTTTCCTGCAAGACTACTGG

|    CDR1       |                  FR2
CTACACATTCACT GGCAACTGGATTGAG TGGATAAAGCAGAGGCCTGGACATGGCCTTGAGTGGATT

|                CDR2                                          |
GGA GAGATCTTACCTGGAAATAGTCGGACTAATTATAATGAAGTTTAAGGGC AAGGCCACTTTCA

FR3
CTGCAGATACATCCTCCAACACAGCCTACATGCAACTCAGCAGCCTGACACCTGAAGACTCTGCCAT

|           CDR3             |            FR4
CTATTTCTGTGCAAGA GTGACTGGGACGTCCTTTGACTACT GGGGCCAAGGCACCACTCTCACAGTC

|
TCCTCT
```

FIG. 2A mAb 2DA6 Amino Acid Sequence

Light chain: Amino acids sequence (128 AA) (SEQ ID NO: 3)

```
|    Leader sequence      |           FR1           |    CDR1     |       FR2
 MDFQVQIFSFLLISASVIMSRG QIVLTQSPAIMSASPGQKVTITC SVSSNIHFMH WYQQKLGFSPK

|  CDR2  |              FR3              |   CDR3    |    FR4     |
 LWIY DTSKLTP GVPARFSGSGSGTSYSLTISSMEAEDAASYFC HQWSSHPHT FGSGTKLEIK
```

Heavy chain: Amino acids sequence (136 AA) (SEQ ID NO: 4)

```
|  Leader sequence   |            FR1             |  CDR1|      FR2
 MDWTWVFLFLLSVTAGVHS QVQLQQSGAELMKPGASVRLSCKTTGYTFT GNWIE WIKQRPGHGLEWI

|         CDR2         |              FR3              |   CDR3    |   FR4
 G EILPGNSRTNYNEKFKG KATFTADTSSNTAYMQLSSLTPEDSAIYFCAR VTGTSFDY WGQGTTLT

|
VSS
```

FIG. 2B

Clone 11C16

Light chain (SEQ ID NO: 5)

```
<-------------------------------- FR1-IMGT ---------------
gagctcgtgctgactcagtcgccctct...gcatctgccgccctgggagcctcggccaag ----------------->               CDR1-IMGT            <-----
ctcacctgcaccctgagcagtgctcacaag..............acctacaccattgca --------------- FR2-IMGT -------------------->            CDR
tggtatcagcaacgggcaggggaggcccctcggtacctgatgcaacttaagagtggg...

2-IMGT          <-----------------------------------------
......ggaacctacaccaaagagaccggtgtccct...gatcgcttctcgggctccagc --------- FR3-IMGT -----------------------------------------
......tctggggctgaccgctacttgatcatctccagcgtccaggttgatgacgaggcc -----------> _____ CDR3-IMGT _____
gactactattgtggtgcagattattctggtggatatgtgttcggcggagggacccagctg
```

Heavy chain (SEQ ID NO: 6)

```
<-------------------------------- FR1-IMGT ---------------
..........................................................

----------------->               CDR1-IMGT            <-----
.tcacctgcaaagcctctggattctccctc............agtgactactggatgaac --------------- FR2-IMGT -------------------->            CDR
tgggtccgccaggctccagggaaggggctggaatggatcggaaccattagtactggt...

2-IMGT          <-----------------------------------------
......ggtagcacatactacacgagctgggcgaaa...ggccgattcaccatctccaaa --------- FR3-IMGT -----------------------------------------
acctcgacc......acggtggatctgcaggtcaccagtccgacaaccgaggacacggcc ----------->                   CDR3-IMGT _____
acctatttctgtgccagagaacatatattcggtggtggctgggatttggatttctggggc
```

FIG. 3A

Clone 9M12

Light Chain (SEQ ID NO: 7)

```
<-------------------------------- FR1-IMGT ---------------
gag...cagctggtggagtccgggggt...cgcctggtcacgcctgggacacccctgaca ----------------->_____ CDR1-IMGT _____<-----
ctcgcctgcacagcctctggattctccctc............agtagccacgacatgatc --------------- FR2-IMGT ------------------->_____ CDR
tgggtccgccaggctccaggggagggactggaatacatcggatacattactgctggt...

2-IMGT _____<--------------------------------------------
......ggtagcccatactacgcgagctgggcaaaa...ggccgattcaccatctccaga --------- FR3-IMGT ------------------------------------------
acctcgacc......acggtggatctgaaaatggccagtctgacaaccgagacacggcca --------->
cgtatttctg Sequence cut short - no CDR3 identified
```

Heavy chain (SEQ ID NO: 8)

```
<-------------------------------- FR1-IMGT ---------------
...........................................................ccctgaca ----------------->_____ CDR1-IMGT _____<-----
ctcgcctgcacagcctctggattctccctc............agtagccacgacatgatc --------------- FR2-IMGT ------------------->_____ CDR
tgggtccgccaggctccaggggagggactggaatacatcggatacattactgctggt...

2-IMGT _____<--------------------------------------------
......ggtagcccatactacgcgagctgggcaaaa...ggccgattcaccatctccaga --------- FR3-IMGT ------------------------------------------
acctcgacc......acggtggatctgaaaatggccagtctgacaaccgaggacacggcc ----------->_____ CDR3-IMGT _____
acgtatttctgtggcagaggtgcttattctggttttggttttgacatctggggcccaggc
```

FIG. 3B

SEQUENCE LISTING

```
<160> NUMBER OF SEQ ID NOS: 9

<210> SEQ ID NO 1
<211> LENGTH: 384
<212> TYPE: DNA
<213> ORGANISM: Mus musculus

<400> SEQUENCE: 1 atggatttc aggtgcagat tttcagcttc ctgctaatca gtgcctcagt cattatgtcc      60
```

```
agaggacaaa ttgttctcac ccagtctcca gcaatcatgt ctgcatctcc agggcagaaa      120
gtcaccataa cctgcagtgt cagctcaaac atacatttca tgcactggta ccagcagaag      180
ttaggattct cccccaaact ctggatttat gacacatcca aactgactcc tggagtccct      240
gctcgcttca gtggcagtgg gtctgggacc tcttactctc tcacaatcag cagcatggag      300
gctgaagatg ctgcctctta tttctgccat cagtggagta gtcacccaca tacgttcgga      360
tcggggacca agctggaaat aaaa                                             384

<210> SEQ ID NO 2
<211> LENGTH: 475
<212> TYPE: DNA
<213> ORGANISM: Mus musculus

<400> SEQUENCE: 2
atggattgga cctgggtctt tctcttcctc ctgtcagtaa ctgcaggtgt ccactcccag       60
gttcagctgc agcagtctgg agctgagctg atgaagcctg gggcctcagt gaggctttcc     120
tgcaagacta ctggctacac attcactggc aactggatta gtggataaaa gcagaggcct     180
ggacatggcc ttgagtggat tggagagatc ttacctggaa atagtcggac taattataat     240
gagaagttta agggcaaggc cactttcact gcagatacat cctccaacac agcctacatg     300
caactcagca gcctgacacc tgaagactct gccatctgca gatacatcct ccaacacagc     360
ctacatgcaa ctcagcagcc tgacacctga agactctgcc atctatttct gtgcaagagt     420
gactgggacg tcctttgact actggggcca aggcaccact ctcacagtct cctct          475

<210> SEQ ID NO 3
<211> LENGTH: 128
<212> TYPE: PRT
<213> ORGANISM: Mus musculus

<400> SEQUENCE: 3

Met Asp Phe Gln Val Gln Ile Phe Ser Phe Leu Leu Ile Ser Ala Ser
  1               5                  10                  15

Val Ile Met Ser Arg Gly Gln Ile Val Leu Thr Gln Ser Pro Ala Ile
                 20                  25                  30

Met Ser Ala Ser Pro Gly Gln Lys Val Thr Ile Thr Cys Ser Val Ser
             35                  40                  45

Ser Asn Ile His Phe Met His Trp Tyr Gln Gln Lys Leu Gly Phe Ser
         50                  55                  60

Pro Lys Leu Trp Ile Tyr Asp Thr Ser Lys Leu Thr Pro Gly Val Pro
 65                  70                  75                  80

Ala Arg Phe Ser Gly Ser Gly Ser Gly Thr Ser Tyr Ser Leu Thr Ile
                 85                  90                  95

Ser Ser Met Glu Ala Glu Asp Ala Ala Ser Tyr Phe Cys His Gln Trp
            100                 105                 110

Ser Ser His Pro His Thr Phe Gly Ser Gly Thr Lys Leu Glu Ile Lys
            115                 120                 125

<210> SEQ ID NO 4
<211> LENGTH: 136
<212> TYPE: PRT
<213> ORGANISM: Mus musculus

<400> SEQUENCE: 4

Met Asp Trp Thr Trp Val Phe Leu Phe Leu Leu Ser Val Thr Ala Gly
  1               5                  10                  15
```

Val His Ser Gln Val Gln Leu Gln Gln Ser Gly Ala Glu Leu Met Lys
            20                  25                  30

Pro Gly Ala Ser Val Arg Leu Ser Cys Lys Thr Thr Gly Tyr Thr Phe
        35                  40                  45

Thr Gly Asn Trp Ile Glu Trp Ile Lys Gln Arg Pro Gly His Gly Leu
    50                  55                  60

Glu Trp Ile Gly Glu Ile Leu Pro Gly Asn Ser Arg Thr Asn Tyr Asn
65                  70                  75                  80

Glu Lys Phe Lys Gly Lys Ala Thr Phe Thr Ala Asp Thr Ser Ser Asn
                85                  90                  95

Thr Ala Tyr Met Gln Leu Ser Ser Leu Thr Pro Glu Asp Ser Ala Ile
            100                 105                 110

Tyr Phe Cys Ala Arg Val Thr Gly Thr Ser Phe Asp Tyr Trp Gly Gln
        115                 120                 125

Gly Thr Thr Leu Thr Val Ser Ser
    130                 135

```
<210> SEQ ID NO 5
<211> LENGTH: 324
<212> TYPE: DNA
<213> ORGANISM: Mus musculus

<400> SEQUENCE: 5
gagctcgtgc tgactcagtc gccctctgca tctgccgccc tgggagcctc ggccaagctc    60
acctgcaccc tgagcagtgc tcacaagacc tacaccattg catggtatca gcaacgggca   120
ggggaggccc ctcggtacct gatgcaactt aagagtgggg gaacctacac caaagagacc   180
ggtgtccctg atcgcttctc gggctccagc tctgggctg accgctactt gatcatctcc    240
agcgtccagg ttgatgacga ggccgactac tattgtggtg cagattattc tggtggatat   300
gtgttcggcg gagggaccca gctg                                          324

<210> SEQ ID NO 6
<211> LENGTH: 269
<212> TYPE: DNA
<213> ORGANISM: Mus musculus

<400> SEQUENCE: 6
tcacctgcaa agcctctgga ttctccctca gtgactactg gatgaactgg gtccgccagg    60
ctccagggaa ggggctggaa tggatcggaa ccattagtac tggtggtagc acatactaca   120
cgagctgggc gaaaggccga ttcaccatct ccaaaacctc gaccacggtg gatctgcagg   180
tcaccagtcc gacaaccgag gacacggcca cctatttctg tgccagagaa catatattcg   240
gtggtggctg ggatttggat ttctggggc                                     269

<210> SEQ ID NO 7
<211> LENGTH: 274
<212> TYPE: DNA
<213> ORGANISM: Mus musculus

<400> SEQUENCE: 7
gagcagctgg tggagtccgg gggtcgcctg gtcacgcctg gacacccct gacactcgcc     60 tgcacagcct ctggattctc cctcagtagc cacgacatga tctgggtccg ccaggctcca   120
ggggagggac tggaatacat cggatacatt actgctggtg gtagcccata ctacgcgagc   180
tgggcaaaag gccgattcac catctccaga acctcgacca cggtggatct gaaaatggcc   240
agtctgacaa ccgagacacg gccacgtatt tctg                               274
```

```
<210> SEQ ID NO 8
<211> LENGTH: 278
<212> TYPE: DNA
<213> ORGANISM: Mus musculus

<400> SEQUENCE: 8
ccctgacact cgcctgcaca gcctctggat tctccctcag tagccacgac atgatctggg      60
tccgccaggc tccaggggag ggactggaat acatcggata cattactgct ggtggtagcc     120
catactacgc gagctgggca aaaggccgat tcaccatctc cagaacctcg accacggtgg     180
atctgaaaat ggccagtctg acaaccgagg acacggccac gtatttctgt ggcagaggtg     240
cttattctgg ttttggtttt gacatctggg gcccaggc                             278

<210> SEQ ID NO 9
<211> LENGTH: 18
<212> TYPE: DNA
<213> ORGANISM: Artificial Sequence
<220> FEATURE:
<223> OTHER INFORMATION: linker

<400> SEQUENCE: 9
ggssrssssg gggsgggg                                                    18
```

FUNGAL DETECTION USING MANNAN EPITOPE

CROSS-REFERENCE TO RELATED APPLICATIONS

The present application is a 35 U.S.C. § 371 national phase application from, and claims priority to, International Application No. PCT/US2016/029085, filed Apr. 23, 2016, which claims priority under 35 U.S.C. § 119(e) to U.S. Provisional Application No. 62/151,865, filed Apr. 23, 2015, all of which are incorporated herein by reference in their entireties.

STATEMENT REGARDING FEDERALLY SPONSORED RESEARCH OR DEVELOPMENT

This invention was made with government support under Grant Nos. R41 AI108114, R41 AI102311, and R33 AI085548 awarded by the National Institutes of Health. The government has certain rights in the invention.

BACKGROUND OF THE INVENTION

Fungi are a global threat to human, animal, plant and environmental health. Fungal skin diseases affect 14% of the global population—approximately 1 billion people. Vulvovaginal candidiasis affects 70-75% of women at least once during their lives. Invasive fungal infections kill about 1.5 million people every year; most deaths are due to *Cryptococcus, Candida, Aspergillus* and *Pneumocystis* species. Fungal infections are also producing biodiversity loss at a global scale; examples include the possible extinction for some species of North American bats due to the ascomycete fungus *Pseudogymnoascus destructans* and amphibians due to the chytrid fungus *Batrachochytrium dendrobatidis*. Fungi have been estimated to cause 72% of all disease-driven extinction/extirpation of animal species and 57% of all disease-driven plant species extinctions/extirpations. Finally, fungal diseases are a major threat to food security. It has been estimated that even low-level persistent fungal disease among five of the most important crops (rice, wheat, maize, potato and soybean) would lead to losses sufficient to feed 8.5% of the world's population. Although unlikely, severe epidemics that would simultaneously affect all five crops would leave food sufficient for only 39% of the world's population.

The methods typically used to diagnosis invasive fungal disease (IFD) in humans are culture, biopsy, radiological imaging, and molecular/serological tests. At present, none of these methods are believed to produce results that that can be attained at or near the patient point-of-care (POC). Tests that may be completed relatively quickly (such as radio-imaging), suffer from a lack of specificity, whereas more specific tests (such as culture) take considerable time to produce a result. At present, antigen detection assays for IFD are limited to *Candida* and *Aspergillus* species (Platelia, Bio-Rad), and neither have gained widespread clinical acceptance. The development of a sensitive/specific POC assay to diagnose IFD would be a major benefit to patients worldwide.

A common feature of strategies to control fungal infections, whether in humans or plants, is the need to rapidly diagnose infection. Early diagnosis and timely use of antifungal agents mitigates the direct impact of infection, prevents the spread of infection, reduces opportunities for development of antibiotic resistance, and controls costs.

Thus, there is a need in the art for novel methods of fungal detection, specifically towards identification of fungi, such as from fungal infection or contamination, in a sample or subject. The present invention satisfies this need.

SUMMARY OF THE INVENTION

As described herein, the present invention relates to compositions and methods for detecting a fungus in a sample. One aspect of the invention includes a method of determining whether a sample contains a fungus. The method comprises contacting a sample to be tested with an antibody that specifically binds the α-1,6 mannose backbone of fungal mannan and assessing specific binding of the antibody to α-1,6 mannose in the sample. When the antibody specifically binds α-1,6 mannose in the sample, the sample contains a fungus.

In another aspect, the invention includes a composition comprising an antibody that specifically binds the α-1,6 mannose backbone of fungal mannan.

In yet another aspect, the invention includes a kit for determining whether a sample contains a fungus, the kit comprising an antibody that specifically binds the α-1,6 mannose backbone of fungal mannan in said sample; and instructional materials for the use thereof.

Still another aspect of the invention includes a method of assessing the efficacy of an antifungal therapy in a subject. The method comprises contacting a first sample from the subject before antifungal therapy is initiated with an antibody that specifically binds the α-1,6 mannose backbone of fungal mannan and assessing specific binding of the antibody to α-1,6 mannose in the first sample; contacting a second sample from the subject after antifungal therapy has been initiated with an antibody that specifically binds the α-1,6 mannose backbone of fungal mannan and assessing specific binding of the antibody to α-1,6 mannose in the second sample. When the level of specific binding of the antibody to α-1,6 mannose in the second sample is less than the level of specific binding of the antibody to α-1,6 mannose in the first sample, the antifungal therapy is effective.

Another aspect of the invention includes a method of assessing the efficacy of an antifungal treatment of a sample comprising a plant, a food or a building material. The method comprises contacting a first sample before antifungal treatment is initiated with an antibody that specifically binds the α-1,6 mannose backbone of fungal mannan and assessing specific binding of the antibody to α-1,6 mannose in the first sample; contacting a second otherwise identical sample after antifungal treatment has been initiated with an antibody that specifically binds the α-1,6 mannose backbone of fungal mannan and assessing specific binding of the antibody to α-1,6 mannose in the second sample. When the level of specific binding of the antibody to α-1,6 mannose in the second sample is less than the level of specific binding of the antibody to α-1,6 mannose in the first sample, the antifungal treatment is effective.

In another aspect, the invention includes a method of making an antibody that specifically binds the α-1,6 mannose backbone of fungal mannan. The method comprises immunizing a mammal with *Saccharomyces* Mnn2, isolating B cells that produce an antibody that specifically binds the α-1,6 mannose backbone of fungal mannan, and fusing the B cells with a cancer cell to generate a hybridoma cell that produces an antibody that specifically binds the α-1,6 mannose backbone of fungal mannan.

In yet another aspect, the invention includes a method of making an antibody that specifically binds the α-1,6 mannose backbone of fungal mannan. The method comprises immunizing a mammal with a substance having an enhanced amount of α-(1→6) mannose, isolating B cells that produce an antibody that specifically binds the α-1,6 mannose backbone of fungal mannan, and fusing the B cells with a cancer cell to make a hybridoma cell that produces an antibody that specifically binds the α-1,6 mannose backbone of fungal mannan.

In another aspect, the invention includes a method of making an antibody that specifically binds the α-1,6 mannose backbone of fungal mannan. The method comprises immunizing a mammal with a fungus comprising an α-1,6 mannose backbone, isolating B cells that produce an antibody that specifically binds the α-1,6 mannose backbone of fungal mannan, and fusing the B cells with a cancer cell to make a hybridoma cell that produces an antibody that specifically binds the α-1,6 mannose backbone of fungal mannan.

In yet another aspect, the invention includes a method of treating a source of a sample determined to have a fungus The method comprises identifying a sample as containing a fungus by contacting a sample to be tested with an antibody that specifically binds the α-1,6 mannose backbone of fungal mannan and assessing specific binding of the antibody to α-1,6 mannose in the sample, wherein when the antibody specifically binds α-1,6 mannose in the sample, the sample contains a fungus, and treating the source of a sample with an antifungal therapy.

In various embodiments of the above aspects or any other aspect of the invention delineated herein, the antibody that specifically binds the α-1,6 mannose backbone of fungal mannan is selected from the group consisting of a monoclonal antibody and a single chain scFv antibody. In another embodiment, the monoclonal antibody is mAb 2DA6. In yet another embodiment, the monoclonal antibody is produced by a hybridoma having ATCC Accession No. PTA-123011. In still another embodiment, the single chain antibody is a single chain scFV antibody. In another embodiment, the single chain antibody is selected from the group consisting of scFv clone 11C16 and scFv clone 9M12.

In another embodiment the sample is selected from the group consisting of a plant, an animal, a building material, and a food.

In yet another embodiment, specific binding of the antibody to α-1,6 mannose is assessed using a method selected from the group consisting of a lateral flow procedure, ELISA, and immunohistopathology.

In still another embodiment, the fungus comprising an α-1,6 mannose backbone is selected from the group consisting of *Aspergillus* spp., *Candida* spp., *Mucor* spp., *Rhizopus* spp., and *Fusarium* spp. In another embodiment, the mammal this is immunized is a Diversity Outbred mouse.

BRIEF DESCRIPTION OF THE DRAWINGS

The following detailed description of preferred embodiments of the invention will be better understood when read in conjunction with the appended drawings. For the purpose of illustrating the invention, there are depicted in the drawings certain embodiments of the invention. However, the invention is not limited to the precise arrangements and instrumentalities of the embodiments depicted in the drawings.

FIGS. 2A-2B show the nucleotide (FIG. 2A) and amino acid (FIG. 2B) sequences of mAb 2DA6 heavy and light chains.

FIGS. 3A-3B show the nucleotide sequences of scFv clones 11C16 and 9M12.

DETAILED DESCRIPTION

Figure 1:
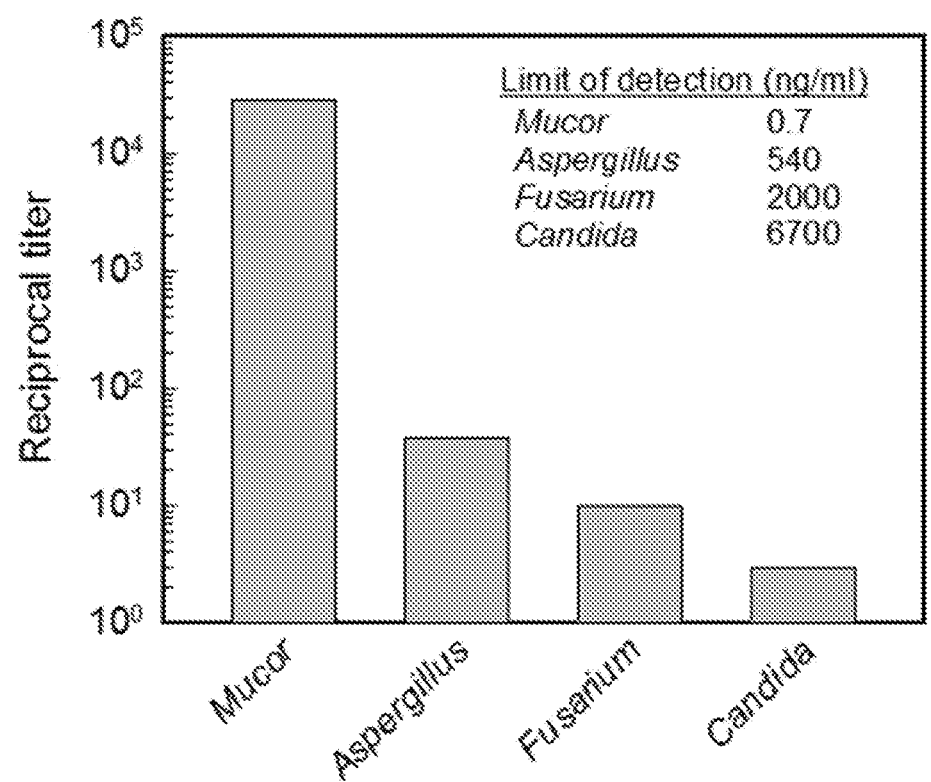
FIG. 1 illustrates the reactivity of mAb 2DA6 with purified mannans of different fungal genera. Results are shown from a sandwich ELISA in which plates were i) coated with mAb 2DA6 to enable mannan capture, ii) incubated with serial dilutions of purified mannan (20 µg/ml starting concentration), and iii) incubated with HRPO-labeled mAb 2DA6. Inset—limit of detection of the sandwich ELISA for mannans isolated from different fungal genera.

This disclosure relates to the field of fungal detection, specifically to the identification of a fungus, such as from fungal infection or contamination, in a sample or subject.

All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Definitions

As used herein, each of the following terms has the meaning associated with it in this section. Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, and organic chemistry are those well-known and commonly employed in the art.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below.

As used herein, the term "about" will be understood by persons of ordinary skill in the art and will vary to some extent on the context in which it is used. As used herein when referring to a measurable value such as an amount, a concentration, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, "animal" refers to living multi-cellular vertebrate organisms, a category that includes, for example, mammals and birds. The term "mammal" includes both human and non-human mammals.

As used herein, "antibody" refers to a polypeptide ligand comprising at least a light chain or heavy chain immunoglobulin variable region which specifically binds an epitope of a polysaccharide, or a fragment of a polysaccharide, or a protein, or a fragment of a protein. Antibodies can include a heavy chain and a light chain, each of which has a variable region, termed the variable heavy (VH) region and the variable light (VL) region. Together, the VH region and the VL region are responsible for binding the antigen recognized by the antibody. This includes intact immunoglobulins and the variants and portions of them well known in the art, such as Fab' fragments, F(ab)'2 fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes recombinant forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, Immunology, 3rd Ed., W.H. Freeman & Co., New York, 1997.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. These fused cells and their progeny are termed "hybridomas." Monoclonal antibodies include humanized monoclonal antibodies.

A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, Antibodies, *A Laboratory Manual*, Cold Spring Harbor Publications, New York (1988), for a description of immunoassay formats and conditions that can be used to determine specific immunoreactivity.

"Antifungal agent" means an agent that inhibits growth of or kills a fungus. Types of antifungal agents that are useful in the present invention include, but are not limited to, tavaborole, nystatin, candicidin, amphotericin B, filipin, bifonazole, albaconazole, and abafungin. Other examples of antifungal agents can be found in Dixon, D. M., & Walsh, T. J. (1996), Chapter 76: Antifungal Agents, *Medical microbiology*, 4th ed. University of Texas Medical Branch at Galveston, Galveston, Tex.

As used herein, "binding" refers to a specific interaction between two or more molecules, such as the binding of an antibody and an antigen (for example an antibody to an antigen). In one embodiment, specific binding is identified by a dissociation constant (Kd). In one embodiment, binding affinity is calculated by a modification of the Scatchard method described by Frankel et al., *Mol. Immunol.*, 16:101-106, 1979. In another embodiment, binding affinity is measured by an antigen/antibody dissociation rate. In yet another embodiment, a high binding affinity is measured by a competition radioimmunoassay (RIA). In several examples, a high binding affinity is at least about $1\times10^{-8}$M. In other embodiments, a high binding affinity is at least about $1.5\times10^{-8}$, at least about $2.0\times10^{-8}$, at least about $2.5\times10^{-8}$, at least about $3.0\times10^{-8}$, at least about $3.5\times10^{-8}$, at least about $4.0\times10^{-8}$, at least about $4.5\times10^{-8}$, or at least about $5.0\times10^{-8}$ M. In one example, the disclosed antibodies have a binding affinity for the antigen of at least 10 nM.

By the term "specifically binds," as used herein, is meant a molecule, such as an antibody or a small molecule, which recognizes and binds to another molecule or feature, but does not substantially recognize or bind other molecules or features in a sample.

As used herein, the terms "comprising," "including," "containing" and "characterized by" are exchangeable, inclusive, open-ended and do not exclude additional, unrecited elements or method steps. Any recitation herein of the term "comprising," particularly in a description of components of a composition or in a description of elements of a device, is understood to encompass those compositions and methods consisting essentially of and consisting of the recited components or elements.

As used herein, the term "consisting of" excludes any element, step, or ingredient not specified in the claim element.

As used herein, the term "consisting essentially of" does not exclude materials or steps that do not materially affect the basic and novel characteristics of the claim.

As used herein, the term "contacting" includes in solution and solid phase, for example contacting a sample with an antibody, for example contacting a sample that contains a polysaccharide of interest such as a polysaccharide associated with a fungal infection.

The terms "effective amount" or "therapeutically effective amount" are used interchangeably herein, and refer to an amount of a compound, formulation, material, or composition, as described herein effective to achieve a particular biological result. Such results may include, but are not limited to, the treatment of a disease or condition as determined by any means suitable in the art. An "antifungal effective amount" refers to an amount of an agent that inhibits growth of or kills a fungus.

"Immunoassay" refers to a biochemical test that measures the presence or concentration of a substance in a sample, such as a biological sample, using the reaction of an antibody to its cognate antigen, for example the specific binding of an antibody to a polysaccharide. Both the presence of antigen or the amount of antigen present can be measured. For measuring polysaccharides, for each the antigen and the presence and amount (abundance) of the polysaccharide can be determined or measured. Measuring the quantity of antigen can be achieved by a variety of methods. One of the most common is to label either the antigen or antibody with a detectable label.

"Instructional material," as that term is used herein, includes a publication, a recording, a diagram, or any other medium of expression which can be used to communicate the usefulness of the composition and/or compound of the invention in a kit. The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

An "individual", "patient" or "subject", as these terms are used interchangeably herein, includes a member of any animal species including, but are not limited to, birds, humans and other primates, and other mammals including commercially relevant mammals such as cattle, pigs, horses, sheep, cats, and dogs. Preferably, the subject is a human.

As used herein, a "label" is detectable compound or composition that is conjugated directly or indirectly to another molecule, such as an antibody or a protein, to facilitate detection of that molecule. Specific, non-limiting examples of labels include fluorescent tags, enzymatic linkages (such as horseradish peroxidase), radioactive isotopes (for example $^{14}C$, $^{32}P$, $^{125}I$, $^{3}H$ isotopes and the like) and particles such as colloidal gold. In some examples a protein, such as a protein associated with a fungus, is labeled with a radioactive isotope, such as $^{14}C$, $^{32}P$, $^{125}I$, $^{3}H$ isotope. In some examples an antibody that specifically binds the polysaccharide is labeled. Methods for labeling and guidance in the choice of labels appropriate for various purposes are discussed for example in Sambrook et al. (Molecular Cloning: A Laboratory Manual 4th Edition, Cold Spring Harbor Laboratory Press, New York, 2012) and Ausubel et al. (In Current Protocols in Molecular Biology, John Wiley & Sons, New York, 2003), Harlow & Lane (Antibodies, *A Laboratory Manual, Cold Spring Harbor Publications, New York,* 2014).

As used herein, "therapeutic agent" refers to a substance that demonstrates some therapeutic effect by restoring or maintaining health, such as by alleviating the symptoms associated with a disease or physiological disorder, or delaying (including preventing) progression or onset of a disease. In some instances, the therapeutic agent is a chemical or pharmaceutical agent, or a prodrug. A therapeutic agent may be an agent which prevents or inhibits one or more signs or symptoms or laboratory findings associated with fungal infection.

A "therapeutically effective amount" or "effective amount" or "therapeutically effective dose" is that amount or dose sufficient to inhibit or prevent onset or advancement, to treat outward symptoms, or to cause regression, of a disease. The therapeutically effective amount or dose also can be considered as that amount or dose capable of relieving symptoms caused by the disease. Thus, a therapeutically effective amount or dose of an anti-fungal agent is that amount or dose sufficient to achieve a stated therapeutic effect. The therapeutically effective amount may vary depending the subject and disease condition being treated, e.g., the weight and age of the subject, the severity of the disease condition, the manner of administration and the like, which can readily be determined by one of ordinary skill in the art.

As used herein, the terms "treatment" and "treating" refer to an approach for obtaining beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The invention includes the discovery of a unique epitope, the α-1,6 mannose backbone of fungal mannan, and an antibody that specifically binds thereto, that can be used to detect the presence of a fungus in a variety of samples across a variety of species of fungus.

Methods are disclosed herein that are used to determine if a sample contains a fungus. Methods are also disclosed that monitor the efficacy of antifungal therapy or treatment. Samples used in the methods are from subjects including humans, animals, plants, food, or building materials. The methods include detecting or determining the level of fungal mannan in the sample. The methods can be conducted over time, to monitor the progression or regression of fungal levels, or to assess the development of fungal infection from a pre-fungal infection condition. The method comprises contacting a sample to be tested with an antibody that specifically binds the α-1,6 mannose backbone of fungal mannan and assessing specific binding of the antibody to α-1,6 mannose in the sample, wherein when the antibody specifically binds α-1,6 mannose in the sample, the sample contains a fungus.

I.) Mannoproteins

A promising biomarker for detection of fungal infection is the mannoprotein located in most fungal cell walls. Immunoassays for fungal mannans or galactomannans have been described for diagnosis of several invasive fungal infections, including candidiasis (Weiner et al., (1976) *J Clin Invest* 58:1045-1053), aspergillosis (Reiss et al., (1979) *Infect Immun* 25:357-365) and histoplasmosis (Wheat et al., (1986) *NEJM* 314:88). The structures of cell wall mannoproteins are best described for the ascomycete yeasts *Saccharomyces cerevisiae* and *Candida* spp., where proteins are decorated with both N- and O-linked sugars. O-linked oligosaccharides consist of one to five mannose units linked to serines and threonines (Strahl-Bolsinger et al., (1999) *Biochim Biophys Acta* 1426:297-307). N-linked glycans have an α-1,6-linked mannose chain of up to 50 mannose residues that extends from the N-glycan core. There are shorter side chains of α-1,2-linked mannose residues that terminate in α-1,3-linked mannose residues (Herscovics et al., (1993) *FASEB J* 7:540-550). Altogether, the N-linked yeast mannan is a highly branched structure with as many as 200 mannose residues. Other fungi such as the ascomycetes *Histoplasma* spp. and *Aspergillus* spp. produce galactomannans that have backbones that include α-1,6-linked mannose but have side chains that include galactose residues (Azuma et al., (1974) *Mycopathol Mycol Appl* 54:111-12, Latgé et al., (1994) *Infect Immun* 62:5424-5433).

The goal of the present study was to identify epitopes of fungal mannans that are shared across the various fungi and to produce an antibody that could serve as a recognition reagent for a "pan-fungal" immunoassay. The results demonstrated herein show that the α-1,6 backbone contains an epitope that is shared across the *Ascomycota* and *Zygomycota* phyla. A mAb (2DA6) that is reactive with this epitope was successfully used to construct an immunoassay that is reactive with a broad range of fungi that produce human or plant disease or that threaten biodiversity. Single chain antibody clone 11C16 was also broadly cross-reactive. whereas scFv clone 9M12 was only reactive with *Candida* mannan.

II) Detecting Fungi in a Sample from a Subject

In one embodiment, there is disclosed a method to determine whether or not a subject has a fungal infection. The type of fungal infection may be an acute or chronic fungal infection. The method comprises contacting a sample to be tested with an antibody that specifically binds the α-1,6 mannose backbone of fungal mannan and assessing specific binding of the antibody to α-1,6 mannose in the sample, wherein when the antibody specifically binds α-1,6 mannose in the sample, the sample contains a fungus.

The sample may include a biological fluid, such as, but not limited to, urine, serum, blood, cerebrospinal fluid (CSF), amniotic fluid, saliva, mucus, or tears. Samples may also include sheddings from the subject, or swabs from skin, scalp, vagina, nasal cavity, oral cavity, fingernails, or toenails. Tissue or cellular material may comprise the sample.

The method of the invention can be used to detect any fungus that expresses the α-1-6 methyltransferase enzyme, an enzyme that catalyzes the formation of α-1,6 mannose in the backbone of fungal mannan. The type of fungi that express α-1-6 methyltransferase include but are not limited to, Zygomyctes and Ascomycetes. Non-limiting examples of human fungal infections include, but are not limited to, invasive fungal disease (IFD), vulvovaginal candidiasis and fungal nail infections. Non-limiting examples of animal fungal infections include, but are not limited to, white-nose syndrome in bats caused by the ascomycete fungus *Pseudogymnoascus destructans* and snake fungal disease caused by the ascomycete *Ophidiomyces ophiodiicola*. In some embodiments, the method includes detecting an increase, such as a statistically significant increase, such as at least a 1.5, 2, 3, 4, or 5 fold increase in the amount of α-1-6 mannose as compared to a reference value. In some embodiments, the method includes detecting a decrease, such as a statistically significant decrease, such as at least a 2, 3, 4, or 5 fold decrease in the amount of α-1-6 mannose as compared to a reference sample.

III.) Detecting Fungi in Plant and Food Samples

In another embodiment, the method of the invention comprises determining whether or not a fungus is present on or in a plant or food sample. The method comprises contacting a sample to be tested with an antibody that specifically binds the α-1,6 mannose backbone of fungal mannan and assessing specific binding of the antibody to α-1,6 mannose in the sample, wherein when the antibody specifically binds α-1,6 mannose in the sample, the sample contains a fungus.

The sample may include plants such as maize, potato, soybean, and fruits. Samples may also include plant-derived food products such as wheat and rice. Other foods including, but not limited to, breads, milk, cheese, cereal, and meat may also comprise the sample.

Non-limiting examples of plant fungal infections include, but are not limited to, rice blast caused by *Magnaporthe oryzae* and grey rot and noble rot: both fungal infections of grapes caused by *Botrytis cinerea*.

IV.) Detecting Fungi in Building Materials:

In yet another embodiment, there is disclosed a method to determine whether or not a fungus is present in a building or building materials. The method comprises contacting a sample to be tested with an antibody that specifically binds the α-1,6 mannose backbone of fungal mannan and assessing specific binding of the antibody to α-1,6 mannose in the sample, wherein when the antibody specifically binds α-1,6 mannose in the sample, the sample contains a fungus.

The sample may include swabs taken from a building material, or a building material itself. Non-limiting examples of building materials include: dry wall, insulation, wood, roof shingles, carpet, tile, laminate flooring, and heating, ventilating, and air conditioning (HVAC) systems. In one non-limiting example, the building material is homogenized in a liquid such as phosphate buffered saline (PBS) and the fungal mannans extracted and subsequently detected.

V) Monitoring

The diagnostic methods of the present invention are valuable tools for practicing physicians, veterinarians, botanists, farmers, or mold remediators so that they may quickly determine the presence of a fungus and take remedial action.

Following the measurement of the expression levels of one or more of the molecules identified herein, the assay results, findings, diagnoses, predictions and/or treatment recommendations are typically recorded and communicated to technicians, physicians and/or patients, for example. In certain embodiments, computers will be used to communicate such information to interested parties, such as, patients and/or the attending physicians. Based on the measurement, the therapy administered to a subject can be modified.

In one embodiment, a diagnosis, prediction and/or treatment recommendation based on the expression level in a test subject of one or more of the fungal infection associated molecules disclosed herein is communicated to the subject as soon as possible after the assay is completed and the diagnosis and/or prediction is generated. The results and/or related information may be communicated to the subject by the subject's treating physician. Alternatively, the results may be communicated directly to a test subject by any means of communication, including writing, such as by providing a written report, electronic forms of communication, such as email, or telephone. Communication may be facilitated by use of a computer, such as in case of email communications. In certain embodiments, the communication containing results of a diagnostic test and/or conclusions drawn from and/or treatment recommendations based on the test, may be generated and delivered automatically to the subject using a combination of computer hardware and software which will be familiar to artisans skilled in telecommunications. One example of a healthcare-oriented communications system is described in U.S. Pat. No. 6,283,761; however, the present disclosure is not limited to methods which utilize this particular communications system. In certain embodiments of the methods of the disclosure, all or some of the method steps, including the assaying of samples, diagnosing of diseases, and communicating of assay results or diagnoses, may be carried out in diverse (e.g., foreign) jurisdictions.

In several embodiments, identification of a human subject as having a fungal infection results in the physician treating the subject, such as prescribing one or more therapeutic agents for inhibiting or delaying one or more signs and symptoms associated with a fungal infection. In another embodiment, identification of an animal subject as having a fungal infection results in the veterinarian treating the animal, such as prescribing one or more therapeutic agents for inhibiting or delaying one or more signs and symptoms associated with a fungal infection. In yet another embodiment, identification of plant as having a fungal infection results in treatment of the plant, such as with one or more therapeutic agents for inhibiting or delaying one or more signs and symptoms associated with a fungal infection. It yet another embodiment, identification of an building material as being contaminated with a fungus results in a treatment, such as spraying with one or more antifungal agents, for inhibiting or delaying one or more signs and symptoms associated with a fungal contamination. In additional embodiments, the dose or dosing regimen is modified based on the information obtained using the methods disclosed herein.

The subject can be monitored while undergoing treatment using the methods described herein in order to assess the efficacy of the treatment protocol. In this manner, the length of time or the amount give to the subject can be modified based on the results obtained using the methods disclosed herein.

VI) Antifungal Therapy

An antifungal agent is any compound that inhibits the growth of or kills a fungus. Such agents may include pharmaceutical fungicides. Examples include but are not limited to tavaborole, nystatin, candicidin, amphotericin B, filipin, bifonazole, albaconazole, and abafungin. Other examples can be found in Dixon, D. M., & Walsh, T. J. (1996), Chapter 76: Antifungal Agents, Medical microbiology, 4th ed. University of Texas Medical Branch at Galveston, Galveston, Tex.

VII). Immunoassays for Diagnosing and Monitoring Fungal Infection

The methods disclosed herein can be performed using various immunoassay formats which are well known in the art. There are two main types of immunoassays, homogeneous and heterogeneous. In homogeneous immunoassays, both the immunological reaction between an antigen and an antibody and the detection are carried out in a homogeneous reaction. Heterogeneous immunoassays include at least one separation step, which allows the differentiation of reaction products from unreacted reagents. A variety of immunoassays can be used to detect one or more of the molecules capable of detecting fungal infection.

ELISA is a heterogeneous immunoassay, which has been widely used in laboratory practice since the early 1970s, and can be used in the methods disclosed herein. The assay can be used to detect protein or polysaccharide antigens in various formats. In the "sandwich" format the antigen being assayed is held between two antibodies. In this method, a solid surface is first coated with a solid phase antibody. The test sample, containing the antigen (e.g., a diagnostic protein), or a composition containing the antigen, such as a urine sample from a subject of interest, is then added and the antigen is allowed to react with the bound antibody. Any unbound antigen is washed away. A known amount of enzyme-labeled antibody is then allowed to react with the bound antigen. Any excess unbound enzyme-linked antibody is washed away after the reaction. The substrate for the enzyme used in the assay is then added and the reaction between the substrate and the enzyme produces a color change. The amount of visual color change is a direct measurement of specific enzyme-conjugated bound antibody, and consequently the antigen present in the sample tested.

ELISA can also be used as a competitive assay. In the competitive assay format, the test specimen containing the antigen to be determined is mixed with a precise amount of enzyme-labeled antigen and both compete for binding to an anti-antigen antibody attached to a solid surface. Excess free enzyme-labeled antigen is washed off before the substrate for the enzyme is added. The amount of color intensity resulting from the enzyme-substrate interaction is a measure of the amount of antigen in the sample tested. A heterogenous immunoassay, such as an ELISA, can be used to detect any molecules associated with fungal infection.

In another example, immuno-PCR can be used to detect any of the molecules associated with fungal infection. Immuno-PCR is a modification of the conventional ELISA format in which the detecting antibody is labeled with a DNA label, and is applicable to the analysis of biological samples (see, e.g., U.S. Pat. No. 5,665,539 and U.S. Patent Application Publication No. 2005/0239108; all herein incorporated by reference). The amplification ability of PCR provides large amounts of the DNA label which can be detected by various methods, typically gel electrophoresis with conventional staining (e.g., Sano et al., *Science*, 258: 120-122, 1992). This method can also include the direct conjugation of the DNA label to the antibody and replacement of gel electrophoresis by using labeled primers to generate a PCR product that can be assayed by ELISA or using real time quantitative PCR. In an example of the real-time PCR method, PCR is used to amplify DNA in a sample in the presence of a nonextendable dual labeled fluorogenic hybridization probe. One fluorescent dye serves as a reporter and its emission spectra is quenched by the second fluorescent dye. The method uses the 5' nuclease activity of Taq polymerase to cleave a hybridization probe during the extension phase of PCR. The nuclease degradation of the hybridization probe releases the quenching of the reporter dye resulting in an increase in peak emission from the reporter. The reactions are monitored in real time.

Homogeneous immunoassays include, for example, the Enzyme Multiplied Immunoassay Technique (EMIT), which typically includes a biological sample comprising the biomarkers to be measured, enzyme-labeled molecules of the biomarkers to be measured, specific antibody or antibodies binding the biomarkers to be measured, and a specific enzyme chromogenic substrate. In a typical EMIT, excess of specific antibodies is added to a biological sample. If the biological sample contains the molecules to be detected, such molecules bind to the antibodies. A measured amount of the corresponding enzyme-labeled molecules is then added to the mixture. Antibody binding sites not occupied by molecules of the protein in the sample are occupied with molecules of the added enzyme-labeled protein. As a result, enzyme activity is reduced because only free enzyme-labeled protein can act on the substrate. The amount of substrate converted from a colorless to a colored form determines the amount of free enzyme left in the mixture. A high concentration of the protein to be detected in the sample causes higher absorbance readings. Less protein in the sample results in less enzyme activity and consequently lower absorbance readings. Inactivation of the enzyme label when the antigen-enzyme complex is antibody-bound makes the EMIT a useful system, enabling the test to be performed without a separation of bound from unbound compounds as is necessary with other immunoassay methods. A homogenous immunoassay, such as an EMIT, can be used to detect any of the molecules associated with fungal infection.

Immunoassay kits are also disclosed herein. These kits include, in separate containers (a) monoclonal antibodies having binding specificity for the polysaccharides used in the diagnosis of fungal infection; and (b) and anti-antibody immunoglobulins. This immunoassay kit may be utilized for the practice of the various methods provided herein. The monoclonal antibodies and the anti-antibody immunoglobulins can be provided in an amount of about 0.001 mg to 100 grams, and more preferably about 0.01 mg to 1 gram. The anti-antibody immunoglobulin may also be a polyclonal immunoglobulin, protein A or protein G or functional fragments thereof, which may be labeled prior to use by methods known in the art. In several embodiments, the immunoassay kit includes one, two, three or four antibodies that specifically bind to molecules associated with fungal infection. The immunoassay kit can also include one or more antibodies that specifically bind to one or more of these molecules. Thus, the kits can be used to detect one or more different molecules associated with fungal infection.

Immunoassays for polysaccharides and proteins differ in that a single antibody is used for both the capture and indicator roles for polysaccharides due to the presence of repeating epitopes. In contrast, two antibodies specific for distinct epitopes are required for immunoassay of proteins. Exemplary samples include biological samples obtained from subjects including, but not limited to, serum and urine samples.

In one particular example, a quantitative ELISA is constructed for detection of fungal associated polysaccharide. These immunoassays utilize mAbs commercially available or disclosed herein. Since a polysaccharide is a polyvalent repeating structure, a single mAb is used for both the capture and indicator phases of an immunoassay. The only requirement is that the mAb have a sufficient affinity. By way of example only, a mAb with an affinity of about 0.5 pM has sufficient affinity.

i) Capture Device Methods

The disclosed methods can be carried out using a sample capture device, such as a lateral flow device (for example a lateral flow test strip) that allows detection of one or more molecules, such as those described herein.

Point-of-use analytical tests have been developed for the routine identification or monitoring of health-related conditions (such as pregnancy, cancer, endocrine disorders, infectious diseases or drug abuse) using a variety of biological samples (such as urine, serum, plasma, blood, saliva). Some of the point-of-use assays are based on highly specific interactions between specific binding pairs, such as antigen/antibody, hapten/antibody, lectin/carbohydrate, apoprotein/cofactor and biotin/(strept)avidin. The assays are often performed with test strips in which a specific binding pair member is attached to a mobilizable material (such as a metal sol or beads made of latex or glass) or an immobile substrate (such as glass fibers, cellulose strips or nitrocellulose membranes). Particular examples of some of these assays are shown in U.S. Pat. Nos. 4,703,017; 4,743,560; and 5,073,484 (incorporated herein by reference). The test strips include a flow path from an upstream sample application area to a test site. For example, the flow path can be from a sample application area through a mobilization zone to a capture zone. The mobilization zone may contain a mobilizable marker that interacts with an analyte or analyte analog, and the capture zone contains a reagent that binds the analyte or analyte analog to detect the presence of an analyte in the sample.

Examples of migration assay devices, which usually incorporate within them reagents that have been attached to colored labels, thereby permitting visible detection of the assay results without addition of further substances are found, for example, in U.S. Pat. No. 4,770,853; WO 88/08534; and EP-A 0 299 428 (incorporated herein by reference). There are a number of commercially available lateral-flow type tests and patents disclosing methods for the detection of large analytes (MW greater than 1,000 Daltons) as the analyte flows through multiple zones on a test strip. Examples are found in U.S. Pat. No. 5,229,073 (measuring plasma lipoprotein levels), and U.S. Pat. Nos. 5,591,645; 4,168,146; 4,366,241; 4,855,240; 4,861,711; 5,120,643; European Patent No. 0296724; WO 97/06439; WO 98/36278; and WO 08/030546 (each of which are herein incorporated by reference). Multiple zone lateral flow test strips are disclosed in U.S. Pat. Nos. 5,451,504, 5,451,507, and U.S. Pat. No. 5,798,273 (incorporated by reference herein). U.S. Pat. No. 6,656,744 (incorporated by reference) discloses a lateral flow test strip in which a label binds to an antibody through a streptavidin-biotin interaction.

In particular examples, the methods disclosed herein include application of a biological sample (such as serum or urine) from a test subject to a lateral flow test device for the detection of one or more molecules (such as one or more molecules associated with fungal infection, for example, combinations of molecules as described above) in the sample. The lateral flow test device includes one or more antibodies (such as antibodies that bind one or more of the molecules associated with fungal infection) at an addressable location. The addressable locations can be, for example, a linear array or other geometric pattern that provides diagnostic information to the user. The binding of one or more molecules in the sample to the antibodies present in the test device is detected and the presence or amount of one or more molecules in the sample of the test subject is compared to a control, wherein a change in the presence or amount of one or more molecules in the sample from the test subject as compared to the control indicates that the subject has a fungal infection.

ii.) Flow-Through Devices

Flow-through type assay devices were designed, in part, to obviate the need for incubation and washing steps associated with dipstick assays. Flow-through immunoassay devices involve a capture reagent (such as one or more antibodies) bound to a porous membrane or filter to which a liquid sample is added. As the liquid flows through the membrane, target analyte (such as protein) binds to the capture reagent. The addition of sample is followed by (or made concurrent with) addition of detector reagent, such as labeled (e.g., gold-conjugated or colored latex particle-conjugated protein). Alternatively, the detector reagent may be placed on the membrane in a manner that permits the detector to mix with the sample and thereby label the analyte. The visual detection of detector reagent provides an indication of the presence of target analyte in the sample. Representative flow-through assay devices are described in U.S. Pat. Nos. 4,246,339; 4,277,560; 4,632,901; 4,812,293; 4,920,046; and 5,279,935; U.S. Patent Application Publication Nos. 20030049857 and 20040241876; and WO 08/030546. Migration assay devices usually incorporate within them reagents that have been attached to colored labels, thereby permitting visible detection of the assay results without addition of further substances. See, for example, U.S. Pat. No. 4,770,853; PCT Publication No. WO 88/08534 and European Patent No. EP-A 0 299 428.

There are a number of commercially available lateral flow type tests and patents disclosing methods for the detection of large analytes (MW greater than 1,000 Daltons). U.S. Pat. No. 5,229,073 describes a semiquantitative competitive immunoassay lateral flow method for measuring plasma lipoprotein levels. This method utilizes a plurality of capture zones or lines containing immobilized antibodies to bind both the labeled and free lipoprotein to give a semi-quantitative result. In addition, U.S. Pat. No. 5,591,645 provides a chromatographic test strip with at least two portions. The first portion includes a movable tracer and the second portion includes an immobilized binder capable of binding to the analyte. Additional examples of lateral flow tests for large analytes are disclosed in the following patent documents: U.S. Pat. Nos. 4,168,146; 4,366,241; 4,855,240; 4,861,711; and 5,120,643; European Patent No. 0296724; WO 97/06439; WO 98/36278; and WO 08/030546.

Devices described herein generally include a strip of absorbent material (such as a microporous membrane), which, in some instances, can be made of different substances each joined to the other in zones, which may be abutted and/or overlapped. In some examples, the absorbent strip can be fixed on a supporting non-interactive material (such as nonwoven polyester), for example, to provide increased rigidity to the strip. Zones within each strip may differentially contain the specific binding partner(s) and/or other reagents required for the detection and/or quantification of the particular analyte being tested for, for example, one or more molecules disclosed herein. Thus these zones can be viewed as functional sectors or functional regions within the test device.

In general, a fluid sample is introduced to the strip at the proximal end of the strip, for instance by dipping or spotting. A sample is collected or obtained using methods well known to those skilled in the art. The sample containing the particular molecules to be detected may be obtained from any biological source. Examples of biological sources include blood serum, blood plasma, urine, spinal fluid, saliva, fermentation fluid, lymph fluid, tissue culture fluid and ascites fluid of a human or animal. In a particular example, the biological source is saliva. The sample may be diluted, purified, concentrated, filtered, dissolved, suspended or otherwise manipulated prior to assay to optimize the immunoassay results. The fluid migrates distally through all the functional regions of the strip. The final distribution of the fluid in the individual functional regions depends on the adsorptive capacity and the dimensions of the materials used.

In some embodiments, porous solid supports, such as nitrocellulose, described hereinabove are preferably in the form of sheets or strips. The thickness of such sheets or strips may vary within wide limits, for example, from about 0.01 to 0.5 mm, from about 0.02 to 0.45 mm, from about 0.05 to 0.3 mm, from about 0.075 to 0.25 mm, from about 0.1 to 0.2 mm, or from about 0.11 to 0.15 mm. The pore size of such sheets or strips may similarly vary within wide limits, for example from about 0.025 to 15 microns, or more specifically from about 0.1 to 3 microns; however, pore size is not intended to be a limiting factor in selection of the solid support. The flow rate of a solid support, where applicable, can also vary within wide limits, for example from about 12.5 to 90 sec/cm (i.e., 50 to 300 sec/4 cm), about 22.5 to 62.5 sec/cm (i.e., 90 to 250 sec/4 cm), about 25 to 62.5 sec/cm (i.e., 100 to 250 sec/4 cm), about 37.5 to 62.5 sec/cm (i.e., 150 to 250 sec/4 cm), or about 50 to 62.5 sec/cm (i.e., 200 to 250 sec/4 cm). In specific embodiments of devices described herein, the flow rate is about 62.5 sec/cm (i.e., 250 sec/4 cm). In other specific embodiments of devices described herein, the flow rate is about 37.5 sec/cm (i.e., 150 sec/4 cm).

Another common feature to be considered in the use of assay devices is a means to detect the formation of a complex between an analyte (such as one or more molecules described herein) and a capture reagent (such as one or more antibodies). A detector (also referred to as detector reagent) serves this purpose. A detector may be integrated into an assay device (for example included in a conjugate pad, as described below), or may be applied to the device from an external source.

A detector may be a single reagent or a series of reagents that collectively serve the detection purpose. In some instances, a detector reagent is a labeled binding partner specific for the analyte (such as a gold-conjugated antibody for a particular protein of interest, for example those described herein).

In other instances, a detector reagent collectively includes an unlabeled first binding partner specific for the analyte and a labeled second binding partner specific for the first binding partner and so forth. Thus, the detector can be a labeled antibody specific for a polysaccharide described herein. The detector can also be an unlabeled first antibody specific for the polysaccharide of interest and a labeled second antibody that specifically binds the unlabeled first antibody. In each instance, a detector reagent specifically detects bound analyte of an analyte-capture reagent complex and, therefore, a detector reagent preferably does not substantially bind to or react with the capture reagent or other components localized in the analyte capture area. Such non-specific binding or reaction of a detector may provide a false positive result. Optionally, a detector reagent can specifically recognize a positive control molecule (such as a non-specific human IgG for a labeled Protein A detector, or a labeled Protein G detector, or a labeled anti-human Ab(Fc)) that is present in a secondary capture area.

a.) Flow-Through Device Construction and Design

A flow-through device involves a capture reagent (such as one or more antibodies) immobilized on a solid support, typically, microtiter plate or a membrane (such as, nitrocellulose, nylon, or PVDF). Characteristics of useful membrane have been previously described; however, it is useful to note that in a flow-through assay capillary rise is not a particularly important feature of a membrane as the sample moves vertically through the membrane rather than across it as in a lateral flow assay. In a simple representative format, the membrane of a flow-through device is placed in functional or physical contact with an absorbent layer (see, e.g., description of "absorbent pad" below), which acts as a reservoir to draw a fluid sample through the membrane. Optionally, following immobilization of a capture reagent, any remaining protein-binding sites on the membrane can be blocked (either before or concurrent with sample administration) to minimize nonspecific interactions.

In operation of a flow-through device, a fluid sample (such as a bodily fluid sample) is placed in contact with the membrane. Typically, a flow-through device also includes a sample application area (or reservoir) to receive and temporarily retain a fluid sample of a desired volume. The sample passes through the membrane matrix. In this process, an analyte in the sample (such as one or more protein, for example, one or more molecules described herein) can specifically bind to the immobilized capture reagent (such as one or more antibodies). Where detection of an analyte-capture reagent complex is desired, a detector reagent (such as labeled antibodies that specifically bind one or more molecules) can be added with the sample or a solution containing a detector reagent can be added subsequent to application of the sample. If an analyte is specifically bound by capture reagent, a visual representative attributable to the particular detector reagent can be observed on the surface of the membrane. Optional wash steps can be added at any time in the process, for instance, following application of the sample, and/or following application of a detector reagent.

b.) Lateral Flow Device Construction and Design

Lateral flow devices are commonly known in the art. Briefly, a lateral flow device is an analytical device having as its essence a test strip, through which flows a test sample fluid that is suspected of containing an analyte of interest. The test fluid and any suspended analyte can flow along the strip to a detection zone in which the analyte (if present) interacts with a capture agent and a detection agent to indicate a presence, absence and/or quantity of the analyte.

Numerous lateral flow analytical devices have been disclosed, and include those shown in U.S. Pat. Nos. 4,313,734; 4,435,504; 4,775,636; 4,703,017; 4,740,468; 4,806,311; 4,806,312; 4,861,711; 4,855,240; 4,857,453; 4,943,522; 4,945,042; 4,496,654; 5,001,049; 5,075,078; 5,126,241; 5,451,504; 5,424,193; 5,712,172; 6,555,390; 6,258,548; 6,699,722; 6,368,876 and 7,517,699; EP 0810436; and WO 92/12428; WO 94/01775; WO 95/16207; and WO 97/06439, each of which is incorporated by reference.

Many lateral flow devices are one-step lateral flow assays in which a biological fluid is placed in a sample area on a bibulous strip (though non-bibulous materials can be used, and rendered bibulous, e.g., by applying a surfactant to the material), and allowed to migrate along the strip until the liquid comes into contact with a specific binding partner (such as an antibody) that interacts with an analyte (such as one or more molecules) in the liquid. Once the analyte interacts with the binding partner, a signal (such as a fluorescent or otherwise visible dye) indicates that the interaction has occurred. Multiple discrete binding partners (such as antibodies) can be placed on the strip (for example in parallel lines) to detect multiple analytes (such as two or more molecules) in the liquid. The test strips can also incorporate control indicators, which provide a signal that the test has adequately been performed, even if a positive signal indicating the presence (or absence) of an analyte is not seen on the strip.

The construction and design of lateral flow devices is very well known in the art, as described, for example, in Millipore Corporation, *A Short Guide Developing Immunochromatographic Test Strips,* 2nd Edition, pp. 1-40, 1999, available by request at (800) 645-5476; and Schleicher & Schuell, *Easy to Work with BioScience, Products and Protocols* 2003, pp. 73-98, 2003, 2003, available by request at Schleicher & Schuell BioScience, Inc., 10 Optical Avenue, Keene, N.H. 03431, (603) 352-3810; both of which are incorporated herein by reference.

Lateral flow devices have a wide variety of physical formats that are equally well known in the art. Any physical format that supports and/or houses the basic components of a lateral flow device in the proper function relationship is contemplated by this disclosure.

Figure 6:
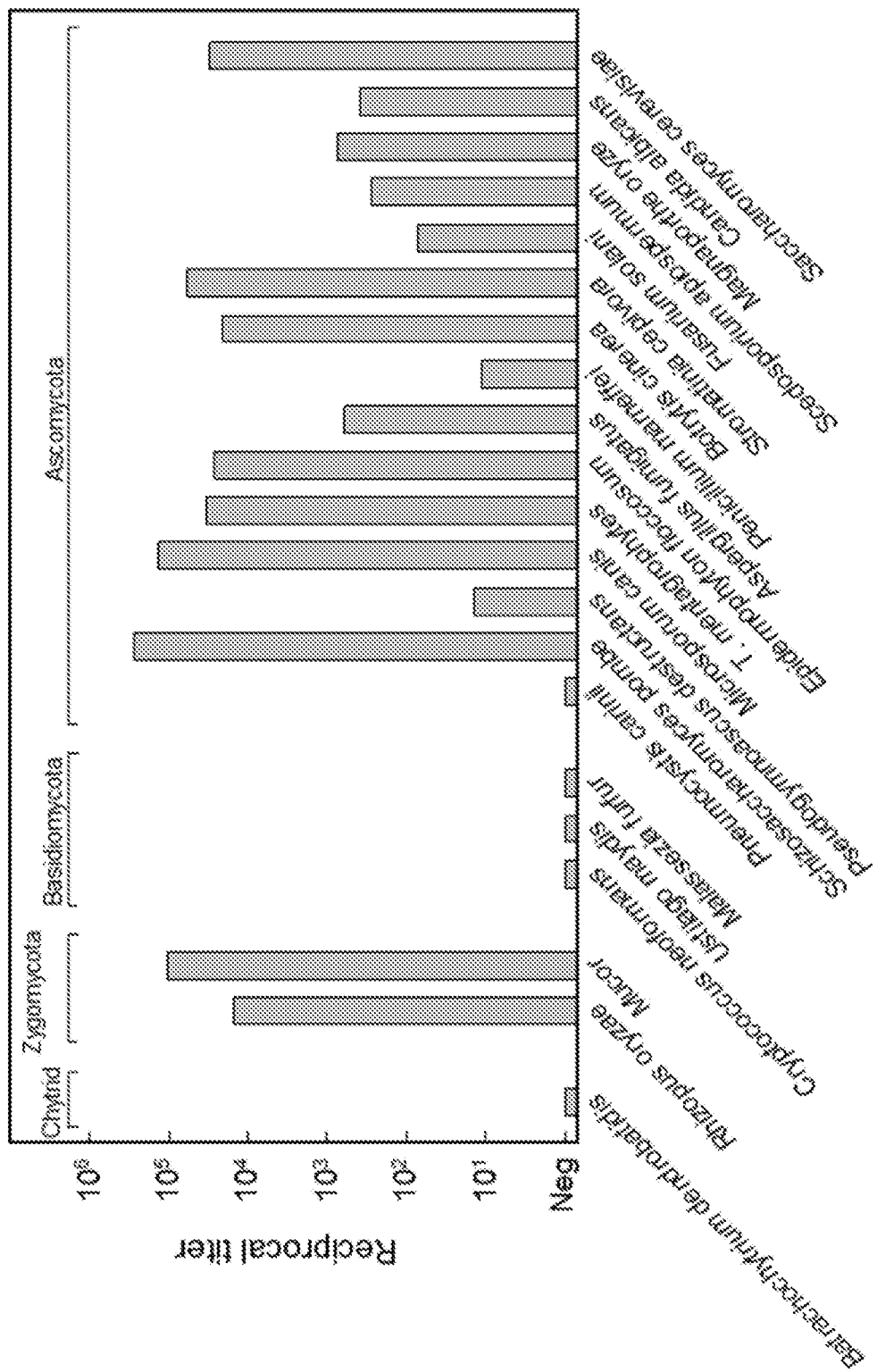
FIG. 6 shows reactivity of cell wall extracts from various fungi in a sandwich ELISA constructed from mAb 2DA6. Cysts of *Pneumocystis carinii* isolated from infected rat lung were used for that fungus. In all other cases, extracts were prepared from mycelia or yeasts from culture.

The basic components of a particular embodiment of a lateral flow device are illustrated in FIG. 6 of U.S. Provisional Patent Application No. 62/151,865, filed Apr. 23, 2015, which is incorporated herein by reference in its entirety. The lateral flow strip is divided into a proximal sample application pad, an intermediate test result zone, and a distal absorbent pad. The flow strip is interrupted by a conjugate pad that contains labeled conjugate (such as gold- or latex-conjugated antibody specific for the target analyte or an analyte analog). A flow path along strip passes from proximal pad, through conjugate pad, into test result zone, for eventual collection in absorbent pad. Selective binding agents are positioned on a proximal test line in the test result membrane. A control line is provided in test result zone, slightly distal to the test line. For example, in a competitive assay, the binding agent in the test line specifically binds the target analyte, while the control line less specifically binds the target analyte.

In operation of the particular embodiment of a lateral flow device illustrated in FIG. 6 U.S. Provisional Patent Application No. 62/151,865, filed Apr. 23, 2015, a fluid sample containing an analyte of interest, such as one or more molecules described herein, is applied to the sample pad. In some examples, the sample may be applied to the sample pad by dipping the end of the device containing the sample pad into the sample (such as serum or urine) or by applying the sample directly onto the sample pad (for example by placing the sample pad in the mouth of the subject). In other examples where a sample is whole blood, an optional developer fluid is added to the blood sample to cause hemolysis of the red blood cells and, in some cases, to make an appropriate dilution of the whole blood sample.

From the sample pad, the sample passes, for instance by capillary action, to the conjugate pad. In the conjugate pad, the analyte of interest, such as a protein or polysaccharide of interest, may bind (or be bound by) a mobilized or mobilizable detector reagent, such as an antibody (such as antibody that recognizes one or more of the molecules described herein). For example, a polysaccharide analyte may bind to a labeled (e.g., gold-conjugated or colored latex particle-conjugated) antibody contained in the conjugate pad. The analyte complexed with the detector reagent may subsequently flow to the test result zone where the complex may further interact with an analyte-specific binding partner (such as an antibody that binds a particular protein, an anti-hapten antibody, or streptavidin), which is immobilized at the proximal test line. In some examples, a polysaccharide complexed with a detector reagent (such as gold-conjugated antibody) may further bind to unlabeled, oxidized antibodies immobilized at the proximal test line. The formation of a complex, which results from the accumulation of the label (e.g., gold or colored latex) in the localized region of the proximal test line is detected. The control line may contain an immobilized, detector-reagent-specific binding partner, which can bind the detector reagent in the presence or absence of the analyte. Such binding at the control line indicates proper performance of the test, even in the absence of the analyte of interest. The test results may be visualized directly, or may be measured using a reader (such as a scanner). The reader device may detect color or fluorescence from the readout area (for example, the test line and/or control line).

In another embodiment of a lateral flow device, there may be a second (or third, fourth, or more) test line located parallel or perpendicular (or in any other spatial relationship) to test line in test result zone. The operation of this particular embodiment is similar to that described in the immediately preceding paragraph with the additional considerations that (i) a second detector reagent specific for a second analyte, such as another antibody, may also be contained in the conjugate pad, and (ii) the second test line will contain a second specific binding partner having affinity for a second analyte, such as a second protein in the sample. Similarly, if a third (or more) test line is included, the test line will contain a third (or more) specific binding partner having affinity for a third (or more) analyte.

1. Sample Pad:

The sample pad is a component of a lateral flow device that initially receives the sample, and may serve to remove particulates from the sample. Among the various materials that may be used to construct a sample pad (such as glass fiber, woven fibers, screen, non-woven fibers, cellosic fibers or paper), a cellulose sample pad may be beneficial if a large bed volume (e.g., 250l/cm$^2$) is a factor in a particular application. Sample pads may be treated with one or more release agents, such as buffers, salts, proteins, detergents, and surfactants. Such release agents may be useful, for example, to promote resolubilization of conjugate-pad constituents, and to block non-specific binding sites in other components of a lateral flow device, such as a nitrocellulose membrane. Representative release agents include, for example, trehalose or glucose (1%-5%), PVP or PVA (0.5%-2%), Tween 20 or Triton X-100 (0.1%-1%), casein (1%-2%), SDS (0.02%-5%), and PEG (0.02%-5%).

2. Membrane and Application Solution:

The types of membranes useful in a lateral flow device (such as nitrocellulose (including pure nitrocellulose and modified nitrocellulose), nitrocellulose direct cast on polyester support, polyvinylidene fluoride, or nylon), and considerations for applying a capture reagent to such membranes have been discussed previously.

3. Conjugate Pad

The conjugate pad serves to, among other things, hold a detector reagent. Suitable materials for the conjugate pad include glass fiber, polyester, paper, or surface modified polypropylene. In some embodiments, a detector reagent may be applied externally, for example, from a developer bottle, in which case a lateral flow device need not contain a conjugate pad (see, for example, U.S. Pat. No. 4,740,468).

Detector reagent(s) contained in a conjugate pad is typically released into solution upon application of the test sample. A conjugate pad may be treated with various substances to influence release of the detector reagent into solution. For example, the conjugate pad may be treated with PVA or PVP (0.5% to 2%) and/or Triton X-100 (0.5%). Other release agents include, without limitation, hydroxypropylmethyl cellulose, SDS, Brij and P-lactose. A mixture of two or more release agents may be used in any given application. In a particular disclosed embodiment, the detector reagent in conjugate pad is a gold-conjugated antibody.

4. Absorbent Pad

The use of an absorbent pad in a lateral flow device is optional. The absorbent pad acts to increase the total volume of sample that enters the device. This increased volume can be useful, for example, to wash away unbound analyte from the membrane. Any of a variety of materials is useful to prepare an absorbent pad, for example, cellulosic filters or paper. In some device embodiments, an absorbent pad can be paper (i.e., cellulosic fibers). One of skill in the art may select a paper absorbent pad on the basis of, for example, its thickness, compressibility, manufacturability, and uniformity of bed volume. The volume uptake of an absorbent made may be adjusted by changing the dimensions (usually the length) of an absorbent pad.

VIII.) Antibody Generation

In certain embodiments, the invention includes a method of making an antibody that specifically binds the α-1,6 mannose backbone of fungal mannan. In one embodiment, the method comprises immunizing a mammal with a fungus comprising an α-1,6 mannose backbone. In another embodiment, the fungi that comprise an α-1,6 mannose backbone are selected from the group consisting of *Aspergillus* spp., *Candida* spp., *Mucor* spp., *Rhizopus* spp., and *Fusarium* spp. In general, fungi of the *Zygomycota* and *Ascomycota* phyla comprise an α-1,6 mannose backbone. Other non-limiting examples of fungi that have an α-1,6 mannose backbone can be found in Tables 4-11 of the disclosure herein.

In another embodiment, the method includes immunizing a mammal with *Saccharomyces* Mnn2. In yet another embodiment, the method includes immunizing a mammal with a substance having an enhanced amount of α-1,6 mannose. Following immunization, splenocytes or B cells that produce an antibody that specifically binds the α-1,6 mannose backbone of fungal mannan are isolated. Hybridomas are generated by fusing the B cells with an immortal/cancer cell.

In some embodiments, antibodies are generated by immunizing a Diversity Outbred mouse. Diversity Outbred mice, also known as DO mice, are from a genetically diverse stock bred at The Jackson Laboratory (www.jax.org/strain/009376). They are commonly known and used by those of ordinary skill in the art.

IV.) Kit

The invention includes a kit that comprises an antibody that specifically binds the α-1,6 mannose backbone of fungal mannan and an instructional material for sue of the same. The kit is useful for detecting the presence of a fungus in a variety of samples across a variety of species of fungus.

The disclosure is illustrated by the following non-limiting Examples.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The materials and methods employed in these experiments are now described.

Fungal Cultures and Infected Tissue:

Sources of all fungal cultures and conditions for growth are provided in Table 12.

eluate was concentrated by ultrafiltration to <2 ml and passed through a 0.22 μm filter. The concentrated Con A eluate was passed over a Superose 12 molecular sieve to remove the alpha-methyl-D-mannopyranoside. A broad peak was produced that adsorbed at 280 nm, indicating the

TABLE 12

Sources of cultures used for study and growth conditions

| Fungus | Strain | Source[a] | Growth conditions | |
|---|---|---|---|---|
| | | | Medium | Temp. |
| Aspergillus fumigatus | ATCC MYA-4609 | ATCC | RPMI 1640, 2% Glucose | 30° C. |
| Batrachochytrium dendrobatidis | CJB5 | J. Voyles | TGhL Media | RT[b] |
| Botrytis cinerea | B05.10 | FGSC | RPMI 1640, 2% Glucose | 25° C. |
| Candida albicans | ATCC MYA-2876 | ATCC | RPMI 1640, 2% Glucose, | 30° C. |
| Cryptococcus neoformans | 602 | T. Kozel | RPMI 1640, 2% Glucose | 30° C. |
| Epidermophyton floccosum | ATCC 38486 | ATCC | RPMI 1640, 2% Glucose | 30° C. |
| Fusarium solani | ATCC 36031 | ATCC | RPMI 1640, 2% Glucose | 30° C. |
| Magnaporthe oryzae | ATCC 201236 | ATCC | RPMI 1640, 2% Glucose | 25° C. |
| Malassezia furfur | ATCC 14521 | ATCC | RPMI 1640, 2% Glucose, 0.1 mg/ml Tween 80 | 30° C. |
| Microsporum canis | ATCC 36299 | Fisher Sci. | RPMI 1640, 2% glucose | 26° C. |
| Mucor circinelloides | ATCC MYA-4072 | ATCC | RPMI 1640, 2% Glucose | 30° C. |
| Penicillium marneffei | ATCC 18224 | ATCC | RPMI 1640, 2% Glucose | RT |
| Pseudogymnoascus destructans | ATCC MYA-4855 | ATCC | RPMI 1640, 2% Glucose | 4-6° C. |
| Rhizopus oryzae | ATCC MYA-3792 | ATCC | RPMI 1640, 2% Glucose | 30° C. |
| Saccharomyces cerevisiae | BY4743 | W. Courchesne | RPMI 1640, 2% Glucose, 40 ug/ml Uridine | 30° C. |
| S. cerevisiae Mnn2 | GE: 33152 | GE | RPMI 1640, 2% Glucose, 40 ug/ml Uridine | 30° C. |
| S. cerevisiae Mnn9 | GE: 32778 | GE | RPMI 1640, 2% Glucose, 40 ug/ml Uridine | 30° C. |
| Scedosporium apiospermum | ATCC MYA-3635 | ATCC | RPMI 1640, 2% Glucose | RT |
| Schizosaccharomyces pombe | ATCC 14548 | ATCC | RPMI 1640, 2% Glucose | 30° C. |
| Stromatinia cepivora | | S. Wang | RPMI 1640, 2% Glucose | RT |
| Trichophytum rubrum | ATCC MYA-4438 | ATCC | RPMI 1640, 2% Glucose | RT |
| Ustilago maydis | ATCC MYA-4924 | ATCC | RPMI 1640, 2% Glucose | 25° C. |

[a]ATCC—American Type Culture Collection; J. Voyles, University of Nevada, Reno; FGSC—Fungal Genetics Stock Center, Kansas State University; T. Kozel, University of Nevada, Reno; Fisher—Fischer Scientific; W. Courchesne, University of Nevada, Reno; S. Wang, Nevada Department of Agriculture
[b]Room temperature Mannan Isolation and Purification from Culture Supernatant Fluids:

Mannan was isolated from cultures of *A. fumigatus, C. albicans, F. solani* and *M. circinelloides*. The length of culture varied with each fungus, ranging from 48 h (*C. albicans*) to 7 days (*Mucor*). Fungal cells were removed from the cultures by filtration through a 0.22 μm filter (Nalgene 585-4520). The *C. albicans* culture required clarification by sedimentation prior to filtration to prevent clogging of the filter. Yeast and mycelia mats were subjected to mechanical disruption using 425-600 μm glass beads (Sigma-Aldrich, St. Louis, Mo.). Sterile water was added to re-suspend fungi, and combined with an equal volume of glass beads. Mechanical disruption was performed for 2 min followed by 5 min of incubation on ice. Five rounds were completed before centrifugation to decant soluble fungal lysate. The culture supernatant fluids and cell lysates were pooled (approximately 5 liters per species) and concentrated to 100 ml with a Millipore Labscale Tangential Flow Filtration System that was fitted with a Pellicon XL 50 cassette.

The concentrated mannans were mixed with an equal volume of 2× Con A binding buffer (40 mM Tris base, 1 M NaCl, 2 mM $MnCl_2$, 2 mM $CaCl_2$, pH 7.4) and applied to a 15 ml column of Concanavalin A-Sepharose 4B that had been equilibrated with 1× Con A binding buffer. Mannans were eluted from the Con A column with 0.5 M alpha-methyl-D-mannopyranoside in 1× binding buffer. The Con A presence of a high molecular weight glycoprotein. The peak was pooled and concentrated by ultrafiltration. The concentration of purified mannan was determined by the phenol-sulfuric acid assay of Dubois, using glucose as a standard.

Glycosyl composition analysis was performed by combined gas chromatography/mass spectrometry (GC/MS) of the per-O-trimethylsilyl (TMS) derivatives of the monosaccharide methyl glycosides, which were produced from each sample by acidic methanolysis.

Extraction of Mannan from Fungal Cultures and Tissues of Fungal-Infected Plants:

Mannan was extracted from intact fungal elements and tissues from infected or healthy plants by the hot citrate method (Peat et al. (1961) *J Chem Soc* 1:29-34). Briefly, cells and tissue were washed with PBS, resuspended in 10 volumes of 19 mM citrate buffer (pH 7.0), and autoclaved for 45 min. The suspension was clarified by centrifugation followed by filtration through a 0.22 μM filter and frozen at −80 C.

mAb Production:

Diversity Outbred mice from Jackson Laboratory (Catalog # J:DO 009376) were hyperimmunized using an immunization schedule based on Refs (Hasenclever et al. (1960) *J Bacteriol* 79:677-681 and Osterland et al. (1966) *J Exp Med* 123:599-614). Briefly, *A. fumigatus* cells were formalin-inactivated, washed in PBS followed by water, bead-beaten, lyophilized, and resuspended in sterile PBS at 1 mg/ml (w/v). Mice were immunized with 100 µl of the *A. fumigatus* cell suspension via the intraperitoneal route every 2 days for a total of 10 injections. Mice were then rested for 4 weeks, after which they received another set of 10 immunizations. Splenocytes from the mice with the highest serum titers against purified *A. fumigatus* galactomannan by ELISA (>100,000) were isolated and cryopreserved as described (Marusich (1998) *J Immunol Methods* 114:155-159). Hybridomas were generated from the cryopreserved splenocytes via standard protocols and were plated at low densities that met the Poisson distribution for monoclonality. All hybridoma wells were initially screened by ELISA for reactivity with purified *A. fumigatus* galactomannan in the solid phase. Hybridomas secreting antibody reactive with *A. fumigatus* galactomannan were expanded and re-screened for continued reactivity with *A. fumigatus* galactomannan as well as for reactivity with purified galactomannan, mannan or fucomannan from *Fusarium* spp., *C. albicans*, and *Mucor* spp, respectively. Hybridomas of interest were subjected to multiple rounds of cloning by limiting dilution to ensure stability and monoclonality.

Production of scFv Reactive with Fungal Mannan:

Rabbits were immunized with whole cells of *C. albicans* using a hyperimmunization schedule based on Refs. (Hasenclever et al. (1960) *J Bacteriol* 79:677-681 and Osterland et al. (1966) *J Exp Med* 123:599-614). Sera from immunized rabbits were evaluated by ELISA using mannan as antigen. Spleens were harvested from rabbits showing the highest anti-mannan titers, and cDNA was isolated from splenic tissue.

First-strand cDNA was synthesized using the Superscript Pre-amplification System with oligo(dT) priming (Invitrogen). Specific oligonucleotide primers covering all known rabbit antibody family sequences were used to amplify VH and VL gene segments separately. The purified variable region products were assembled into scFv format by overlapping PCR. An 18 amino acid linker fragment (GGSSRSSSSGGGGSGGGG)(SEQ ID NO:9) was used to connect the VL and VH fragments. The final DNA fragments, which encoded a library of scFv antibody fragments (VL-linker-VH), were gel purified, digested with SfiI, and cloned into the appropriately cut phagemid vector pADL23b (Antibodies Design Laboratories, San Diego, Calif.). The recombinant phagemid was introduced into competent XL1Blue *Escherichia coli* by electroporation. The phage library was panned against immobilized *Candida* mannan using a solid-phase protocol. Forty eight scFv phage clones were randomly selected (from the appropriate output plate) for ELISA to evaluate their binding activity against *Candida* mannan. HRP-conjugated anti-M13 mAb (GE Healthcare Life Sciences, Pittsburgh, Pa.) was used for detection. All clones with a significant signal above background were further analyzed for specificity and uniqueness using BstO1 restrictive enzyme digestion. *Candida*-specific and pan-fungal-specific clones were further analyzed for gene family using Sanger Sequencing results in the international ImMunoGeneTics information system (IMGT.org). Reactivity of the scFv phage clones with different fungal mannans was done using purified mannans in the solid phase and HRP-conjugated anti-M13 mAb as an indicator of scFv phage binding.

Quantitative Antigen-Capture ELISA:

Microtiter plates were coated overnight with mAb 2DA6 (10 µg/ml) in coating buffer (100 mM carbonate, pH 9.6), washed with PBS-Tween (PBS containing 0.05% Tween 20), and blocked for 60 min at 37° C. with blocking buffer (PBS containing 0.5% Tween+5% w/v powdered milk). Samples of purified mannan (starting concentration of 20 µg/ml) or hot citrate extracts from fungal cultures or infected or control tissue were serially diluted in blocking buffer and incubated for 60 min at 37° C. with the mAb-coated wells. Plates were washed with blocking buffer, incubated for 60 min at 37° C. with horseradish peroxidase-labeled mAb 2DA6 (2 µg/ml) diluted in blocking buffer, washed with PBS-Tween and then incubated with tetramethylbenzidine substrate (Kirkegaard & Perry Laboratories, Inc., Gaithersburg, Md.). The reaction was stopped after 30 min with a solution of 1 M $H_3PO_4$ and plates were read at an optical density of 450 nm ($OD_{450}$). The dilution of purified mannan or sample extract that produced an OD of 0.5 in a log-log plot of $OD_{450}$ vs. dilution or ng mannan/ml was calculated as the endpoint. Depending on the experimental design, results were reported as the sample dilution at the endpoint (titer) or as the minimal concentration of purified mannan that produce the endpoint OD (limit of detection).

Lateral Flow Immunoassay:

The typical LFIA contains at least four zones: sample receiving zone, labelling zone, capture zone and receiving zone. The sample receiving zone is designed for accepting the sample fluid. A common membrane may be used for both the sample receiving zone and the labelling zone, or they may employ separate membranes. The labelling zone contains mAb 2DA6 labelled with an indicator particle where the target analyte is labelled. The capture zone may employ a separate membrane containing a 2DA6 test line where the labelled target analyte is captured. The capture zone also includes an additional control line to verify proper flow between membranes. The receiving zone uses an absorbent membrane to act as a reservoir for excess fluid that has flowed through the capture zone.

For the mannan LFIA, the sample receiving zone and labelling zone were constructed using a Fusion 5 membrane (GE Healthcare). The membrane was treated with a solution containing BSA and Triton X for 2 minutes and then dried in a 37° C. oven for 1 hour. For the labelling zone, mAb 2DA6 was passively absorbed to 40 nm colloidal gold particles, blocked with a solution of bovine serum albumin and concentrated to produce a final $OD_{540nm}$=10. The capture zone was prepared by using a BioDot XYZ3050 non-contact dispenser to spray the 2DA6 mAb test line and goat anti-mouse Ig control line at 1 mg/ml in phosphate buffered saline onto Hi-Flow Plus HF120 (EMD Millipore) nitrocellulose membrane at 1 µl/cm. The nitrocellulose membrane was then dried for 30 min at 37° C. The prepared membranes and an absorbent wicking pad were overlapped and assembled using an adhesive backing card, and then cut into 4 mm wide test strips.

Immediately before testing, 5 µl of the gold conjugated 2DA6 was applied to the labelling zone of an assay. Forty microliters of each fungal extract sample were then applied to the sample receiving zone, and the test strip was placed in a microtiter well containing 150 µl of 1% casein in PBS. After 15 minutes, test and control lines were visually evaluated and digital images were collected.

Bioinformatics Analysis for Presence of Enzymes Involved in Synthesis of α-1,6-Linked Mannose Backbone:

A BLASTp search was performed against the NCBI non-redundant protein database, which includes all non-redundant GenBank CDS translations as well as all PDB, SwissProt, PIR and PRF sequences. BLASTp algorithm parameters were set to default, which included a word size of 3. The query sequence was Mnn9p from *Saccharomyces cerevisiae* (Uniprot accession number P39107). The search set was limited to the indicated fungi. The search set was broadened to the indicated fungal genus in cases where the genome of a selected fungal species had not been sequenced yet.

Periodate Oxidation and Protease Digestion:

Periodate oxidation was performed as described (Woodward et al., (1985) *J Immunol Methods* 78:143-153). Briefly, purified mannan at 1 mg/ml was combined with an equal volume of 40 mM sodium meta-periodate (or water for mock treated samples) for 1 hr at 4° C. The sodium meta-periodate solution was prepared in water. Samples were then dialyzed against water to remove excess periodate and any formaldehyde formed during the reaction, followed by reductive amination with an equal volume of 2% w/v glycine to block the aldehydes. Protease digestion was performed by incubating purified mannan with Proteinase K at a final concentration of 0.9 mg/ml mannan and 1 mg/ml Proteinase K for 1 hr at 55° C. Samples were then boiled for 10 min to heat-inactivate the Proteinase K. Mock-digested mannan was prepared in an identical manner except the Proteinase K was not included.

Surface Plasmon Resonance—Affinity and Kinetic Determination:

Binding experiments were performed using a BIAcore X100 (GE Healthcare, Piscataway, N.J.). Affinity constants were determined using the steady state model, and the kinetics were determined using the Bivalent binding algorithm (GE Lifesciences Biacore Assay Handbook). The running and sample buffer used for all experiments was HBS buffer, pH 7.4, containing 10 mM HEPES, 150 mM NaCl, 3 mM EDTA, and 0.05% surfactant P20, filtered and degassed (HBS-EP+). Purified fungal mannans from *Mucor* spp., *Aspergillus fumigatus*, *Fusarium* spp., and *Candida albicans* were immobilized, using standard amine coupling, onto a CM5 sensor chip for 1080 sec or until immobilization levels of 3000 response units (RU) were reached. A flow cell was left unmodified for reference subtraction. To evaluate binding, samples were diluted in HBS-EP+ and analyzed at several concentrations ranging between 1-200 µg/ml. At each concentration, mAb 2DA6 was injected over the modified chip surface at 30 µl/min for 180 sec. The chip surface was regenerated between runs with a 1 min pulse of 4 M MgCl$_2$.

Identification of a mAb with Broad Reactivity Across Fungal Mannans

Mice were immunized with whole cells of *A. fumigatus* in an effort to produce mAbs that were reactive with fungal mannan. Splenocytes were harvested from mice that produced high levels of antimannan antibodies, and hybridomas were prepared using standard technologies. Numerous colonies were found to produce antibodies that were reactive with *A. fumigatus* galactomannan mannan. All positive colonies were given a second screen to assess the extent of reactivity of mAbs with mannans from other fungi, i.e., *Mucor* spp., *Fusarium* spp. and *Candida albicans* (Table 1). A broad spectrum of cross-reactivity patterns was observed among the hybridomas, with some mAbs only reactive with *A. fumigatus* galactomannan. Other mAbs showed reactivity with two or more of the different mannans. Two mAbs were reactive with mannan of all four fungi, suggesting a pan-fungal reactivity. One of the broadly reactive mAbs (mAb 2DA6) proved to be a robust cell line in culture and produced copious amounts of antibody. This mAb was chosen for further study. The nucleotide sequences for the light chain (SEQ ID NO: 1) and heavy chain (SEQ ID NO: 2) of mAb 2DA6 are shown in FIG. 2A. The amino acid sequences for the light chain (SEQ ID NO: 3) and heavy chain (SEQ ID NO: 4) of mAb 2DA6mAb 2DA6 are shown in FIG. 2B. The hybridoma (2DA6 3B11) that produces mAb 2DA6 was deposited to ATCC Accession No. PTA-123011 on Apr. 8, 2016.

TABLE 1

IgG subclass and spectrum of mannan reactivity of mAbs produced in response to immunization with *Aspergillus fumigatus* cellular antigen

| | Hybridoma cell line | | | | | | | | | | |
|---|---|---|---|---|---|---|---|---|---|---|---|
| Mannan | 4EE9 | 1AG7 | 1AC1 | 1CD6 | 3AE6 | 2BG2 | 2AG9 | 4AF11 | 3ED9 | 1AD7 | 2DA6 |
| *A. fumigatus* | + | + | + | + | + | + | + | + | + | + | + |
| *Mucor* spp. | − | − | − | − | + | − | + | + | + | + | + |
| *Fusarium* spp. | − | − | + | + | − | + | + | + | − | + | + |
| *C. albicans* | − | − | − | − | − | − | − | − | + | + | + |
| IgG subclass | IgG1 | IgG2b | IgG1 | IgG2b | IgG2b | IgG2b | IgG3 | IgG1 | IgG2b | IgG1 | IgG1 |

An initial experiment was done to determine the extent to which mAb 2DA6 was reactive with mannans from different fungi. Mannans were isolated from *Mucor* spp., *Aspergillus fumigatus*, *Fusarium* spp. and *Candida albicans*. These fungal mannans were chosen for study because the composition of the mannans reflected the known diversity of mannan structure, i.e., fucomannan [*Mucor* (Miyazaki et al., (1980) In Sandford Pa., Matsuda K (ed), *Fungal polysaccharides*, Symposium Series no 126)], galactomannan [*A. fumigatus* (Latge et al. (1994) *Infect Immun* 62:5424-5433)] and mannan [*C. albicans* (Kobayashi et al. (1989) *ArchBiochem Biophys* 272:364-375.)]. Before study, the glycosyl content of mannans isolated from each of the different fungi was assessed. In every case, the composition was consistent with the expected composition, e.g., mannan, galactomannan or fucomannan (Table 2).

TABLE 2

Glycosyl composition of purified mannans.

| Fungi | Mannose (%) | Galactose (%) | Fucose (%) | Other sugars |
|---|---|---|---|---|
| *Mucor* spp. | 57 | 2.4 | 41 | Trace |
| *C. albicans* | 99 | 1.2 | None | None |
| *Fusarium* spp. | 88 | 12 | None | None |
| *A. fumigatus* | 92 | 8.5 | None | None | mAb binding was evaluated by use of a sandwich ELISA in which microtiter plates were first coated with unlabeled mAb 2DA6. The wells were then incubated with varying amounts of each mannan. Capture of the mannans was determined by use of enzyme-linked (horseradish peroxidase, HRPO) mAb 2DA6. The results (FIG. 1) showed that each mannan was captured in the sandwich ELISA. However, the sensitivity of the sandwich ELISA for detection of the mannans was highly variable, with the relative order of sensitivity: *Mucor*>*Aspergillus*>*Fusarium*>*Candida*.

Identification of an scFv with Broad Reactivity Across Fungal Mannans

Production of scFvs via phage display was also evaluated as a means to produce anti-mannan antibodies. To this end, rabbits were immunized with whole cells of *C. albicans* to produce synthetic antibodies reactive with fungal mannans. Splenocytes were harvested from rabbits that produced high levels of antimannan antibodies, and scFvs were produced using phage display technology.

The VH and VL genes of splenocytes were amplified using DNA primers that are specific to immunoglobulins. Overlap PCR was used to assemble a full-length scFv (VH-peptide linker-VL). Using these constructs, a library containing $1\times10^7$ unique *E. coli* transformants was generated. Five rounds of bio-panning using mannan in the solid phase were completed to enrich for a pool of scFv that reacted with *Candida* mannan. ELISA using mannan in the solid phase was completed on polyclonal bacteriophage that were isolated after each round of panning. Signal increase, relative to a non-specific antigen (bovine serum albumin), was observed following each round of bio-panning through pan 4; after that, background binding increased.

Monoclonal scFvs were isolated by choosing 48 colonies from the output titer plates of pan round 4. Small-scale phage preparations showed that 41/48 scFv reacted with the mannan of *Candida* but not bovine serum albumin. The remaining 41 colonies were analyzed by digesting the pADL23b plasmid with BstO1, which showed 13 unique digestion patterns. Genetic analysis by DNA sequencing confirmed that unique V-D-J (VH) and V-J (VL) were present for 10 of the clones. These clones showed varying reactivity with the mannans of *Candida albicans* and other fungal species (illustrated in Table 3). One scFv (11C16) showed reactivity with the mannans of *Candida*, *Aspergillus* and *Mucor*. Sequences of the scFv for the highly reactive *Candida*-specific clone 9M12 (SEQ ID NOs: 7-8) and the broadly pan-fungal reactive clone 11C16 (SEQ ID NOs: 5-6) are shown in FIGS. 3A-3B.

α-1,6-Linked Mannose in the Mannan Backbone is Required for mAb 2DA6 Binding mAb 2DA6 was chosen for further evaluation and immunoassay construction based on i) its strong binding across fungal genera, ii) robust growth and mAb synthesis in cell culture, and iii) production of antibody of the IgG1 subclass. The IgG1 subclass is typically easy to isolate from hybridoma supernatant fluid and shows no tendency for self-association that might produce background in immunoassays.

A common structural feature of mannans of *Rhizopus, Mucor, Aspergillus* and *Candida* species is the presence of an α-1,6-linked mannose residue in the backbone, to which side chains are linked that may contain mannose, fucose and/or galactose (Miyazaki et al., (1980) In Sandford Pa., Matsuda K (ed), *Fungal polysaccharides*, Symposium Series no 126), (Latge et al. (1994) *Infect Immun* 62:5424-5433), and (Kobayashi et al. (1989) *ArchBiochem Biophys* 272:364-375). Presence of this common backbone structure, despite considerable variability in side chain structure, suggested that a component of the mannan backbone is the epitope that is recognized by mAb 2DA6.

There is an extensive set of *S. cerevisiae* mannosylation mutants that would allow for evaluation of the contribution of various structural elements of yeast mannan to binding by mAb 2DA6. Specifically, Mnn9p is a component of the mannan polymerization complexes M-Pol I and M-Pol II which are required for extension of the α-1,6-mannose backbone (Jungmann et al., (1998) EMBO J 17:423-434). Mnn9 mutants produce a highly truncated α-1,6-mannose backbone. Mnn2p attaches the initial α-1,2-mannose unit that branches off from the α-1,6-mannose backbone (Gopal (1987), *Proc Natl Acad Sci USA* 84:8824-8828). Mnn2 mutants produce an unbranched α-1,6-mannose chain that is capped with a single α-1,2-linked mannose (Jungmann et al., (1999) *J Biol Chem* 274:6579-6585).

Figure 4:
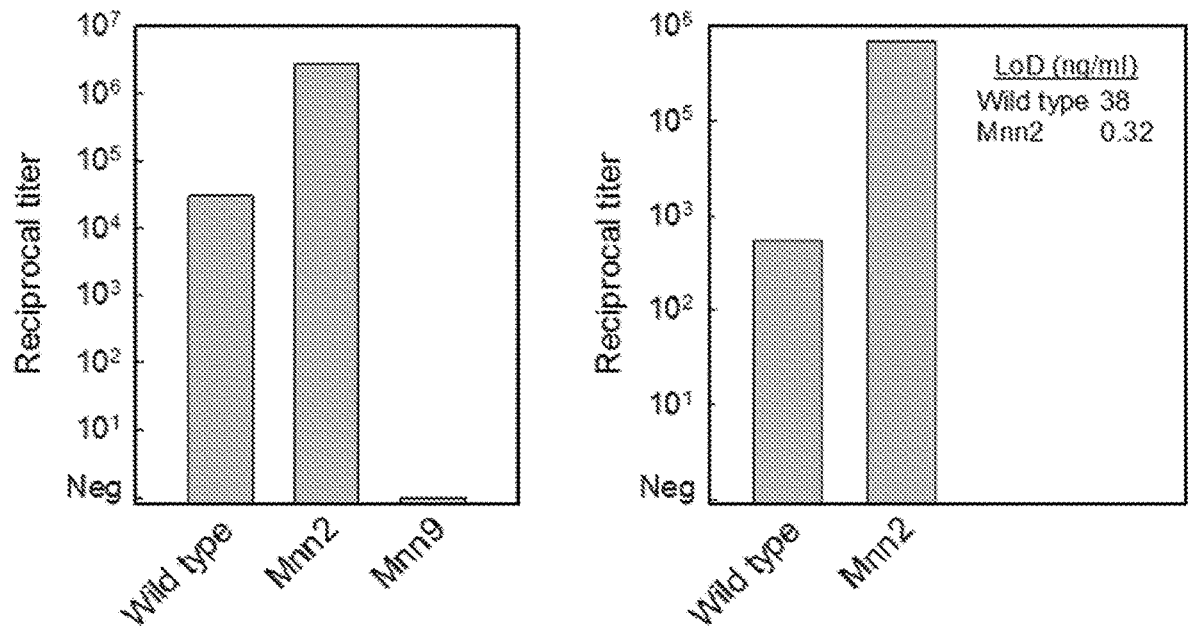
FIG. 4 illustrates the reactivity of mAb 2DA6 with mannans of the parental wildtype and mannan mutants of *S. cerevisiae*. Left panel—a sandwich ELISA constructed from mAb 2DA6 was used to assess reactivity of cell extracts from the parental wild type and Mnn2 and Mnn9 mutants. Right panel—reactivity of purified wild type and Mnn2 mannans in the sandwich ELISA. The starting concentration for the purified mannans was 20 µg/ml. Inset—limit of detection of the sandwich ELISA for mannans isolated from the parental wild type and Mnn2 mutant strains.

Hot citrate extracts were prepared from the parental *S. cerevisiae* BY4773 strain (mannan produced by BY4773 is termed wild type for the purposes of this report) and the Mnn2 and Mnn9 mutants. Extracts were evaluated using the sandwich ELISA constructed from mAb 2DA6. The results showed no reactivity with extracts from the Mnn9 mutant strain. In contrast, there was a 93-fold increase in the titer of extract from the Mnn2 mutant compared to extract from the parental strain (FIG. 4—left panel).

The difference in titers between extracts from the Mnn2 mutant and the parental strain could be due to intrinsic differences in ability of the mannans to be captured in the sandwich ELISA or to differences in production or extractability of mannan from the yeast cells. As a consequence, mannan was purified from hot citrate extracts of the Mnn2 mutant and the parental strains. Examination of the reactivity of the two mannans in the sandwich ELISA showed that there was a 130-fold higher titer for mannan from the Mnn2 mutant relative to wild type mannan from the parental strain (FIG. 4—right panel). Indeed, sandwich ELISA showed a greater sensitivity for detection for Mnn2 mannan (limit of detection=0.32 ng/ml) than for mannans of all other fungi examined in FIG. 1.

Figure 5:
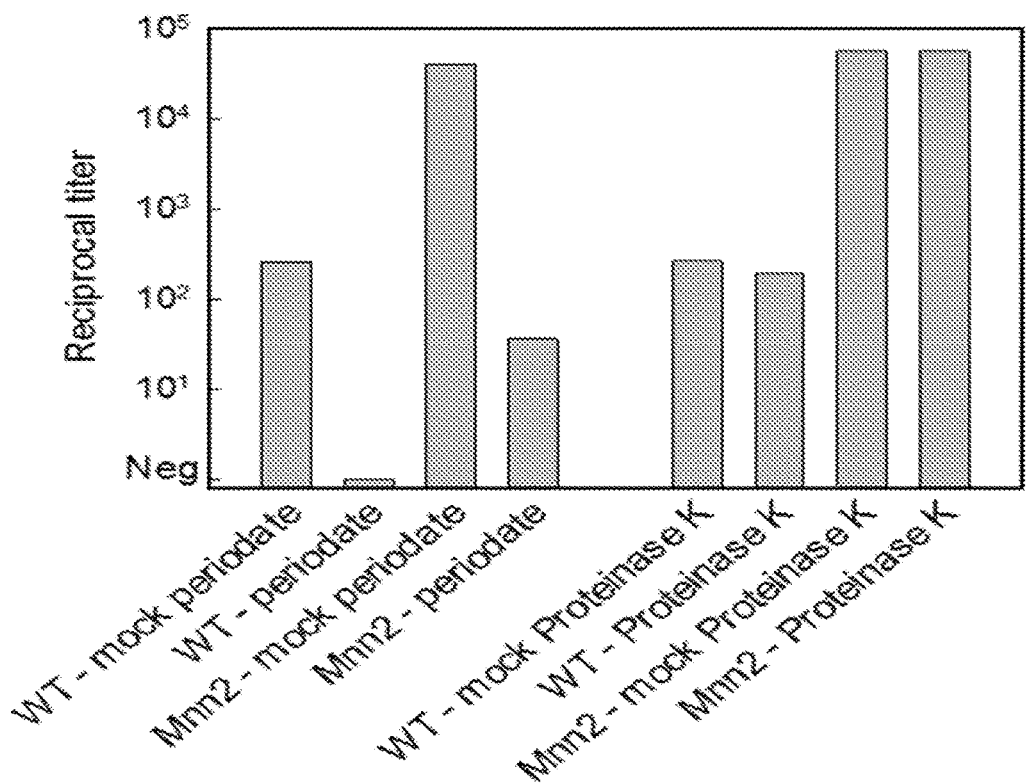
FIG. 5 illustrates the effect of treatment of wild type (WT) and Mnn2 mannan with periodate and Proteinase K on reactivity with mAb 2DA6 in a sandwich ELISA. Mannans were mock-treated with all reagents except periodate or Proteinase K or were treated with each reagent.

Yeast mannans are components of cell wall glycoproteins that are modified with both N-linked and O-linked glycans. This raises a question as to the relative contribution of the carbohydrate and protein segments to binding by mAb 2DA6. Mild periodate oxidation at acid pH cleaves carbohydrate vicinal hydroxyl groups without altering the structure of polypeptide chains (Hay et al., (1965), *Meth Carb Chem* 5:357-361). Treatment of both wildtype and Mnn2 mutant yeast mannan with periodate led to a >99% loss of reactivity with mAb 2DA6 in the sandwich ELISA constructed from mAb 2DA6 (FIG. 5). In contrast, treatment of the two mannanoproteins with Proteinase K had no effect on reactivity of either mannan with mAb 2DA6 in the sandwich ELISA (FIG. 5).

Surface Plasmon Resonance—Affinity and Kinetic Determination

The binding properties of mAb 2DA6 were determined by SPR (Table 13). A bivalent binding algorithm was used to determine the on ($k_a$)- and off ($k_d$)-rates of mAb binding. Calculated $K_D$ ranged from 260-710 nM, depending on the fungal mannan that was used for analysis.

TABLE 13

Analysis of parameters for binding of mAb 2DA6 to fungal mannans by surface plasmon resonance

| Mannan | Bivalent binding kinetics | | |
|---|---|---|---|
| | $K_D$ (nM) | $k_a$ ($M^{-1}s^{-1}$) | $k_d$ ($s^{-1}$) |
| *Mucor* spp. | 260 | $25 \times 10^3$ | $13 \times 10^{-3}$ |
| *Aspergillus fumigatus* | 400 | $13 \times 10^3$ | $8 \times 10^{-3}$ |
| *Fusarium* spp. | 320 | $32 \times 10^3$ | $7 \times 10^{-3}$ |
| *Candida albicans* | 710 | $8 \times 10^3$ | $32 \times 10^{-3}$ |

Bioinformatics Analysis for Enzymes Involved in Synthesis of α-1,6-Linked Mannose Backbone Two α-1,6-mannosyltransferase complexes (M-Pol I and M-Pol II) extend the α-1,6-linked mannan backbone of *S. cerevisiae* (Jungmann et al. (1998) EMBO J 17:423-434, Jungmann et al. (1999) J Biol Chem 274:6579-6585). Mnn9p is a key component of both complexes. Because mAb 2DA6 recognizes yeast α-1,6-linked mannan (FIG. 4), it was hypothesized that fungal species that contained protein sequence(s) with significant homology to Mnn9p from *S. cerevisiae* would be reactive with mAb 2DA6. Thus, a BLASTp analysis was performed for the fungal species of interest using *S. cerevisiae* Mnn9p as the query to search the NCBInr protein database, which includes all non-redundant GenBank CDS translations as well as all PDB, SwissProt, PIR and PRF sequences. Alignments with expect values smaller than $1e^{-30}$ were considered significant. Fungi that were evaluated included one member of the *Chytridiomycota*, two zygomycetes, three basidiomycetes and 13 ascomytetes, including *Pneumocystis* spp. The results (Table 4) showed no homologues among any of the chytridomycetes or basidiomycetes. In contrast, there were *S. cerevisiae* Mnn9p homologues for both of the zygomycetes (*Rhizopus* and *Mucor*) and 11 of the 12 ascomycetes for which there were enough sequences for analysis. The only exception was *Pneumocystis* spp. which did not have a Mnn9p homologue.

TABLE 3

Specificity of rabbit scFvs.

| Mannan | Rabbit scFv | | | | |
|---|---|---|---|---|---|
| | 1C9 | 5C19 | 9M12 | 11C16 | 4M10 |
| *C. albicans* | +++ | ++ | +++ | +++ | ++ |
| *Aspergillus* | – | – | – | + | – |
| *Mucor* | – | – | – | ++ | – |

Direct experimentation was done to validate the in silico predictions of mAb 2DA6 reactivity. Hot citrate extracts were prepared from cultures of most fungi shown in Table 4, including the chytridiomycete *Batrachochytrium dendrobatidis*, two zygomycetes, three basidiomycetes, and 13 members of the *Ascomycota* phylum. In the case of *Pneumocystis* spp., extracts were prepared from organisms purified from infected rat lung. The extracts were evaluated for reactivity in the sandwich ELISA constructed from mAb 2DA6. The results (FIG. 6) showed complete agreement between the experimental results and results predicted from the bioinformatics analysis for the presence of Mnn9p homologues. Specifically, extracts from the *B. dendrobatidis* isolate and three different members of the *Basidiomycota* (*Cryptococcus neoformans*, *Ustilago maydis* and *Malassezia furfur*) failed to react in the sandwich ELISA. In contrast, extracts from both fungi of the Zygomycota (*Rhizopus* and *Mucor*) were highly reactive. Similarly, 12 of 13 extracts from the *Ascomycota* were reactive. Extracts from *P. carinii* purified from lung of infected rats were negative.

TABLE 4

Relationship between fungal taxonomy and production of the mAb 2DA6 epitope

| Phylum/Subphylum/Class | Genus/species | Disease | Mnn9 homology[a] | mAb 2DA6 reactivity with cell extract |
|---|---|---|---|---|
| Chytridiomycota | | | | |
| Chytridiomycetes | *Batrachochytrium dendrobatidis* | Chrytridiomycosis in amphibians | None | No |
| Zygomycota | | | | |
| Mucormycotina | *Rhizopus oryzae* | Mucormycosis | 6e–69[b] | Yes |
| | *Mucor* spp. | Mucormycosis | 1e–67[b] | Yes |
| Basidiomycota | | | | |
| Agaricomycotina | | | | |
| Tremellomycetes | *Cryptococcus neoformans* | Cryptococcosis | None | No |
| Ustilaginomycotina | | | | |
| Ustilaginomycetes | *Ustilago maydis* | Corn smut | None | No |
| Exobasidiomycetes | *Malassezia furfur* | Tinea versicolor | None[b] | No |
| Ascomycota | | | | |
| Taphrinomycotina | | | | |
| Pneumocystidomycetes | *Pneumocystis* spp. | Pneumocystis pneumonia | None[b] | No |
| Schizosaccharomycetes | *Schizosaccharomyces pombe* | Fission yeast - not a pathogen | 2e–109 | Yes |

TABLE 4-continued

Relationship between fungal taxonomy and production of the mAb 2DA6 epitope

| Phylum/Subphylum/Class | Genus/species | Disease | Mnn9 homology[a] | mAb 2DA6 reactivity with cell extract |
|---|---|---|---|---|
| Pezizomycotina | | | | |
| Dothideomycetes | *Pseudogymnoascus destructans* | Bat white-nose disease | 1e−83 | Yes |
| Eurotiomycetes | *Microsporum canis* | Dermatophytosis/onychomycosis | 2e−113 | Yes |
| | *Trichophyton rubrum* | Dermatophytosis/onychomycosis | 1e−117 | Yes |
| | *Epidermophyton floccosum* | Dermatophytosis | ND[c] | Yes |
| | *Aspergillus fumigatus* | Invasive aspergillosis | 2e−119 | Yes |
| | *Penicillium manrneffei* | Penicilliosis | 6e−119 | Yes |
| Leotiomycetes | *Botrytis cinerea* | Grey rot and noble rot | 3e−111 | Yes |
| | *Stromatinia cepivora* | White rot in *Allium* species | | Yes |
| Sordariomycetes | *Fusarium solani* species complex | Sea turtle hatch failure; fungal keratitis; fusariosis | 1e−119 | Yes |
| | *Scedosporium apiospermum* | Scedosporiosis; mycetoma | 2e−113 | Yes |
| | *Magnaporthe oryzae* | Rice blast disease | 9e−118 | Yes |
| Saccharomycotina | | | | |
| Saccharomycetes | *Saccharomyces cerevisiae* | Not normally a pathogen | N/A | Yes |
| | *Candida albicans* | Invasive and mucosal candidiasis | 8e−148 | Yes |

[1]BLASTp Expect value;; <1e−30 was considered significant.
[b]BLASTp analysis of all NCBInr sequences from indicated genus.
[c]ND - Too few sequences in NCBI database for homology search
[d]N/A - not applicable. *S. cerevisiae* was the Mnn9 sequence source for all homology testing Predicted Reactivity of mAb 2DA6 with Fungi of Importance for Animal, Human, Agricultural or Environmental Health Fungi pose threats to animal, human, agricultural and environmental health. As a consequence, a bioinformatics search for Mnn9p homologues was done to predict the likely reactivity of mAb 2DA6 with common fungal threats to global well-being (Tables 5-11). The results show probable reactivity with 7/10 of the major causes of plant pathology (Table 5), 9/10 major invasive human fungal infections (Table 6), 8/10 cutaneous and subcutaneous fungal infections (Table 7), 4/6 examples of fungi responsible for large-scale biodiversity loss (Table 8), 5/7 of fungal-driven extinction and extirpation events in plants and animals (Table 9), 6/7 fungal agents of food and agricultural spoilage (Table 10), and 9/10 fungi commonly found in water-damaged building materials (Table 11).

TABLE 5

Predicted reactivity of mAb 2DA6 with major fungal pathogens in plant pathology[a]

| Fungus | Disease | Phylum | Accession # | Mnn9 homology Homology | Predicted reactivity with mAb 2DA6 |
|---|---|---|---|---|---|
| *Magnaporthe oryzae* | Rice blast | Ascomycota | XP_003718954.1 | 9e−118 | Yes |
| *Botrytis cinerea* | Necrotropic fungus; many hosts | Ascomycota | XP_001556212.1 | 3e−111 | Yes |
| *Puccinia* spp | Rust diseases on wheat | Basidiomycota | | None | No |
| *Fusarium graminearum* | Head blight of wheat | Ascomycota | XP_011326511.1 | 5e−116 | Yes |
| *Fusarium oxysporum* | Fusarium wilt; many hosts | Ascomycota | EXA49808.1 | 1e−116 | Yes |
| *Blumeria graminis* | Powdery mildew of grasses | Ascomycota | EPQ65832.1 | 4e−110 | Yes |
| *Mycosphaerella graminicola* | Septoria tritici blight of wheat | Ascomycota | XP_003857008.1 | 4e−126 | Yes |

TABLE 5-continued

Predicted reactivity of mAb 2DA6 with major fungal pathogens in plant pathology[a]

| Fungus | Disease | Phylum | Mnn9 homology Accession # | Homology | Predicted reactivity with mAb 2DA6 |
|---|---|---|---|---|---|
| *Colletotrichum* spp. | Multiple diseases; multiple hosts | Ascomycota | ENH88330.1 | 3e−117 | Yes |
| *Ustilago maydis* | Corn smut | Basidiomycota | | None | No |
| *Melampsora lini* | Flax rust | Basidiomycota | | ND[b] | No |

[a]Fungi selected from (Dean et al., (2012) *Mol Plant Pathol* 13: 414-430.
[b]Not determined; too few sequences in NCBI database for homology search.

TABLE 6

Predicted reactivity of mAb 2DA6 with most common fungal causes of invasive fungal infection in humans[a]

| Fungus | Disease | Phylum | Mnn9 homology Accession # | Homology | Predicted reactivity with mAb 2DA6 |
|---|---|---|---|---|---|
| *Cryptococcus neoformans* | Cryptococcosis | Basidiomycota | | None | No |
| *Candida albicans* | Invasive candidiasis | Ascomycota | XP_716624.1 | 8e−148 | Yes |
| *Pneumocystis jirovecii* | Pneumocystis pneumonia | Ascomycota | | None | Indeterminated[d] |
| *Aspergillus* spp. | Aspergillosis | Ascomycota | XP_001273073.1 | 1e−124[b] | Yes |
| *Coccidioides immitis* | Coccidioidomycosis | Ascomycota | XP_001246370.1 | 4e−120 | Yes |
| *Histoplasma capsulatum* | Histoplasmosis | Ascomycota | EGC49211.1 | 9e−119 | Yes |
| *Rhizopus* and *Mucor* spp. | Mucormycosis | Zygomycota | CEG79707.1 | 9e−69[c] | Yes |
| *Penicillium marneffei* | Penicilliosis | Ascomycota | XP_002143795.1 | 6e−119 | Yes |
| *Paracoccidioides brasiliensis* | Paracoccidioidomycosis | Ascomycota | XP_010758816.1 | 1e−115 | Yes |
| *Blastomyces dermatitidis* | Blastomycosis | Ascomycota | XP_002622725.1 | 3e−118 | Yes |

[a]Fungi selected from (Brown et al., (2012) *Sci Transl Med* 4: 165rv113.
[b]Results are shown for a search of the genus *Aspergillus*.
[c]The protein sequence with the greatest similarity (that shown) is from *Rhizopus*.
[d]Discrepancy between location of fungus in the Ascomycota phylum and absence of an Mnn9 homologue must be resolved by direct experimentation. In the case of *P. carinii*, direct experimentation did, in fact, determine that the fungus does not make a mannan with mAb 2DA6 reactivity (FIG. 6)

TABLE 7

Predicted reactivity of mAb 2DA6 with significant fungal causes of skin, hair, nail, eye, cutaneous and subcutaneous fungal infections in humans[a]

| Fungus | Disease | Phylum | Mnn9 homology Accession # | Homology | Predicted reactivity with mAb 2DA6 |
|---|---|---|---|---|---|
| *Trichophyton* spp. | Dermatophytosis (ringworm) | Ascomycota | XP_003238615.1 | 3e−117 | Yes |
| *Microsporum* spp. | Dermatophytosis (ringworm) | Ascomycota | XP_003176649.1 | 1e−117 | Yes |
| *Epidermophyton floccosum* | Dermatophytosis (ringworm) | Ascomycota | | ND[b] | Probable[c] |
| *Malassezia* spp. | Tinea versicolor | Basidiomycota | | None | No |
| *Candida albicans* | Candida vaginitis | Ascomycota | XP_716624.1 | 8e−148 | Yes |
| *Fusarium* spp. | Fungal keratitis | Ascomycota | XP_003051726.1 | 3e−118 | Yes |
| *Sporothrix schenckii* | Sporotrichosis | Ascomycota | ERT03180.1 | 1e−110 | Yes |

TABLE 7-continued

Predicted reactivity of mAb 2DA6 with significant fungal causes of skin, hair, nail, eye, cutaneous and subcutaneous fungal infections in humans[a]

| Fungus | Disease | Phylum | Mnn9 homology Accession # | Homology | Predicted reactivity with mAb 2DA6 |
|---|---|---|---|---|---|
| *Fonsecaea* spp. | Chromoblastomycosis | Ascomycota | KIY00514.1 | 2e−118 | Yes |
| *Madurella mycetomatis* | Eumycetoma | Ascomycota | | None | Indeterminate[d] |
| *Bipolaris* spp. | Subcutaneous phaeohyphomycosis | Ascomycota | XP_007705235.1 | 5e−116 | Yes |

[a]Fungi selected from chapters in (Bennett J E, Dolin R, Blaser M J. (2015). Mandell Douglas and Bennett's principles and practice of infectious diseases, 8th ed. Elsevier Saunders)
[b]Not determined; too few sequences in NCBI database for homology search.
[c]Designation as "probable" is based on location of the fungus in the Ascomycota phylum, but lack of sufficient sequences in the NCBI database precludes confirmation of of presence Mnn9p homologue.
[d]Discrepancy between location of fungus in the Ascomycota phylum and absence of an Mnn9 homologue must be resolved by direct experimentation.

TABLE 8

Predicted reactivity of mAb 2DA6 with major fungal causes of potential biodiversity loss[a]

| Fungus | Disease | Phylum | Mnn9 homology Accession # | Homology | Predicted reactivity with mAb 2DA6 |
|---|---|---|---|---|---|
| *Batrachochytrium dendrobatidis* | Chytridiomycosis in amphibians | Chytridiomycota | | None | No |
| *Ophidiomyces ophiodiicola* | Snake fungal disease | Ascomycota | | ND[b] | Probable[c] |
| *Pseudogymnoascus destructans* | Bat white-nose disease | Ascomycota | XP_012740031.1 | 1e−83 | Yes |
| *Aspergillus sydowii* | Sea fan aspergillosis | Ascomycota | XP_001273073.1[d] | 1e−124 | Yes |
| *Nosema* spp. | Bee colony collapse disorder | Microsporidia | | None | No |
| *Fusarium solani* species complex | Hatch failure in sea turtles | Ascomycota | XP_003051726.1 | 1e−119 | Yes |

[a]Fungi selected in part from (Fisher et al., (2012) *Nature* 484: 186-194).
[b]Not determined; too few sequences in NCBI database for homology search.
[c]Designation as "probable" is based on location of the fungus in the Ascomycota phylum, but lack of sufficient sequences in the NCBI database precludes confirmation of presence of Mnn9p homologue.
[d]Results are shown for a search of the genus *Aspergillus*.

TABLE 9

Predicted reactivity of mAb 2DA6 with agents of fungal disease-driven and regional extirpation events across animal and plant tax[a]

| Fungus | Disease | Phylum | Mnn9 homology Accession # | Homology | Predicted reactivity with mAb 2DA6 |
|---|---|---|---|---|---|
| *Batrachochytrium dendrobatidis* | Amphibian extinction/extirpation | Chytridomycota | | None | No |
| *Geomyces destructans* | Bat extirpation | Ascomycota | XP_012740031.1 | 1e−83 | Yes |
| *Steinhausia* sp. | Hawaiian tree snail extinction | Microsporidia | | ND[b] | No |
| *Cryphonectria parasitica* | Chestnut tree extirpation | Ascomycota | | ND | Probable[c] |
| *Ophiostoma* spp. | Elm tree extirpation | Ascomycota | EPE06315.1[c] | 5e−108 | Yes |
| *Fusarium circinatum* | Monterey pine extirpation | Ascomycota | XP_003051726.1[c] | 3e−118 | Yes |

TABLE 9-continued

Predicted reactivity of mAb 2DA6 with agents of fungal disease-driven and regional extirpation events across animal and plant tax[a]

| Fungus | Disease | Phylum | Mnn9 homology | | Predicted reactivity with mAb 2DA6 |
| --- | --- | --- | --- | --- | --- |
| | | | Accession # | Homology | |
| Pestalotiopsis spp. | Florida torreya extinction (~99%) | Ascomycota | XP_007827205.1[c] | 5e−113 | Yes |

[a] Fungi selected from (Fisher et al., (2012) Nature 484: 186-194).
[b] Not determined; too few sequences in NCBI database for homology search.
[c] Designation as "probable" is based on location of the fungus in the Ascomycota phylum, but lack of sufficient sequences in the NCBI database precludes confirmation of presence of Mnn9p homologue.
[e] Search done at genus level.

TABLE 10

Predicted reactivity of mAb 2DA6 with selected fungal agents of food and agricultural spoilage[a]

| Fungus | Disease | Phylum | Mnn9 homology | | Predicted reactivity with mAb 2DA6 |
| --- | --- | --- | --- | --- | --- |
| | | | Accession # | Homology | |
| Rhizopus spp. | Vegetables and fruits; bread mold | Zygomycota | CEG79707.1 | 6e−69 | Yes |
| Botrytis cinerea | Soft fruits | Ascomycota | XP_001556212.1 | 3e−111 | Yes |
| Cladosporium spp. | Grains | Ascomycota | | ND[b] | Probable[c] |
| Alternaria spp. | Grains, fruit | Ascomycota | | None | Indeterminate[d] |
| Fusarium spp. | Grains | Ascomycota | XP_003051726.1 | 3e−118 | Yes |
| Penicillium spp. | Grains, fruit | Ascomycota | CEJ56560.1 | 9e−124 | Yes |
| Aspergillus spp. | Grains | Ascomycota | XP_001273073.1 | 1e−124 | Yes |

[a] Fungi selected from (Lacey (1989) Soc Appl Bacteriol Symp Ser 18: 11S-25S, Filtenborg et al. (1996) Int J Food Microbiol 33: 85-102).
[b] Not determined; too few sequences in NCBI database for homology search.
[c] Location of fungus in the Ascomycota phylum and the absence of sufficient sequence in NCBI database only allows for prediction of "probable."
[d] Discrepancy between location of fungus in the Ascomycota phylum and absence of an Mnn9 homologue must be resolved by direct experimentation.

TABLE 11

Predicted reactivity of mAb 2DA6 with fungal genera commonly found on water-damaged building materials[a]

| Fungus | Phylum | Mnn9 homology | | Predicted reactivity with mAb 2DA6 |
| --- | --- | --- | --- | --- |
| | | Accession # | Homology | |
| Penicillium spp. | Ascomycota | CEJ56560.1 | 9e−124 | Yes |
| Aspergillus spp. | Ascomycota | XP_001273073.1 | 1e−124 | Yes |
| Chaetomium spp. | Ascomycota | XP_006696111.1 | 9e−118 | Yes |
| Acremonium spp. | Ascomycota | | ND[b] | Probable[c] |
| Ulocladium spp. | Ascomycota | | ND[b] | Probable[c] |
| Cladosporium spp. | Ascomycota | | ND[b] | Probable[c] |
| Mucor spp. | Zygomycota | EPB85583.1 | 1e−67 | Yes |
| Trichoderma spp. | Ascomycota | KUE99899.1 | 3e−120 | Yes |
| Alternaria spp. | Ascomycota | | None | Indeterminate[d] |
| Sporothrix spp. | Ascomycota | ERT03180.1 | 2e−110 | Yes |

[a] Fungi selected from (Andersen et al.(2011) Appl Environ Microbiol 77: 4180-4188).
[b] Not determined; too few sequences in NCBI database for homology search.
[c] Location of fungus in the Ascomycota phylum and the absence of sufficient sequence in NCBI database only allows for prediction of "probable."
[d] Discrepancy between location of fungus in the Ascomycota phylum and absence of an Mnn9 homologue must be resolved by direct experimentation.

Lateral Flow Immunoassay for Detection of Fungal Mannan

The sandwich ELISA format used for studies in FIGS. 1, 4 and 5 has the advantages of high sensitivity and generation of quantitative results. However, the ELISA format takes several hours to complete and requires skilled laboratory personnel and considerable laboratory infrastructure. In contrast, the lateral flow immunoassay platform (LFIA) produces a rapid result (15 min) and is well-suited for point-of-need use. As a consequence, a LFIA was constructed from mAb 2DA6 and was used to assay mannans in extracts from selected fungi that were predicted to have Mnn9p homologues and were shown by experimental results to be reactive in the sandwich ELISA constructed from mAb 2DA6 (FIG. 6).

Figure 7:
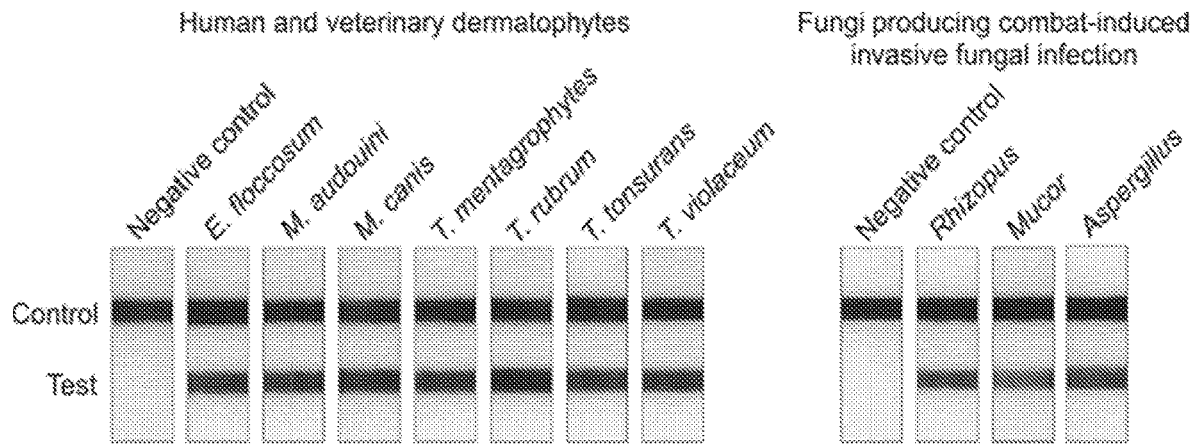
FIG. 7 illustrates detection of mannan in culture extracts from medically relevant fungi in a lateral flow immunoassay (LFIA) constructed from mAb 2DA6. Left panel-extracts from cultures of *Epidermophyton* spp., *Microsporum* spp. and *Trichophyton* spp. that cause dermatophyte infection in humans and animals. Right panel—extracts from cultures of fungi that produce combat-induced invasive fungal infection. Negative control—citrate buffer.

In one example, extracts were prepared from cultures of seven fungi that produce dermatophyte infection in humans and animals. The results showed a high level of reactivity that was similar across the various dermatophytes (FIG. 7-left panel). In the second example, extracts were prepared from cultures of the most common fungi producing trauma-induced invasive fungal infection (IFI), i.e., members of the order Mucorales and *Aspergillus* spp. Mannan was readily detectable by LFIA analysis of extracts from all of the IFI fungi tested.

Figure 8:
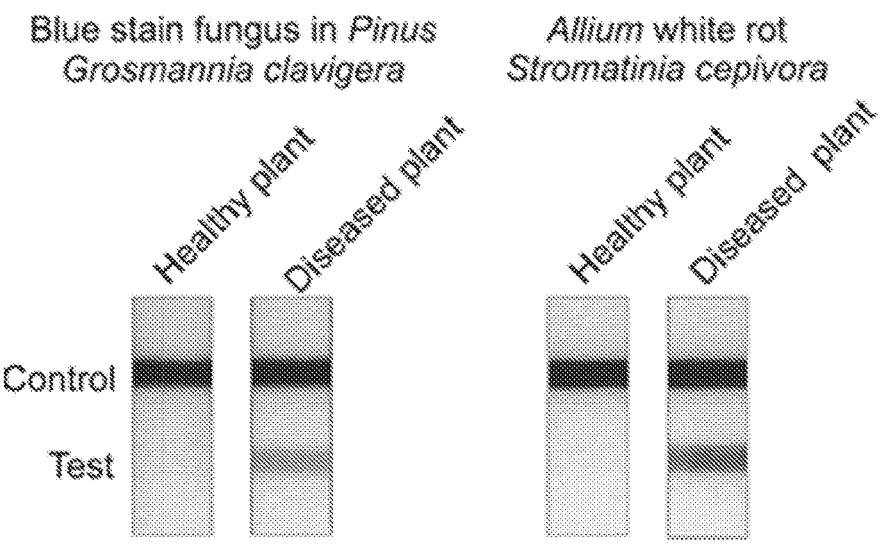
FIG. 8 shows use of LFIA constructed from mAb 2DA6 to detect mannan in extracts from tissue of *Pinus contorta* (lodgepole pine) infected with *Grosmannia clavigera* [blue stain fungus (left)] and tissue from *Allium* species (onion) infected with *Stromatinia cepivora* [*Allium* white rot (right)]. Results are shown for extracts from healthy and diseased plants.

LFIA can also be used to detect fungal mannan in extracts from infected tissue. In one example, an extract was prepared from healthy *Allium cepa* (common onion) or *Allium* infected with Album white rot (*Stromatinia cepivora*). In another example, an extract was prepared from healthy *Pinus contorta* (lodgepole pine) or *Pinus* infected with blue stain fungus (*Grosmannia clavigera*). The results showed a positive result using tissue from infected plants and no reaction using tissue from healthy plants (FIG. 8).

In the present study, a mAb was produced that can address the question: is it a fungus? Results herein indicate that the test will detect the presence of fungi of the *Zygomycota* and *Ascomycota*, but not fungi of the *Chytridiomycota* or *Basidiomycota*. Importantly, ascomycetes and zygomycetes account for almost all of invasive, cutaneous and subcutaneous human fungal infections, most plant pathogens, and most fungi that threaten environmental health (Tables 5-11).

All available evidence indicates that the epitope recognized by mAb 2DA6 is located on the α-1,6 backbone of cell wall mannan. First, where structures have been published, mAb 2DA6 was reactive with purified mannans (FIG. 1) or cell extracts of fungi (FIG. 6) whose cell wall mannans have backbones i) comprised primarily or entirely of α-1,6 mannose. e.g., *S. cerevisiae, C. albicans, Mucor* and *Rhizopus*, and the dermatophytes or ii) have mannans where α-1,6 mannose is a significant component of the backbone, e.g., *A. fumigatus*. Second, mAb 2DA6 is reactive with wild type yeast mannan and mannan from a Mnn2 mutant (FIG. 4), but extracts of a Mnn9 mutant were not reactive. Mnn9 mutants do not form the multi-protein complex having α-1,6-mannosyl transferase activity and are unable to form the long α-1,6-linked backbone of yeast mannan. In contrast, Mnn2 mutants are unable to add the initial α-1,2-mannose unit that branches off the α-1,6-mannose backbone. Mnn2 mutants would produce an unbranched α-1,6-mannose chain that is capped with a single α-1,2-linked mannose. The fact that a sandwich ELISA showed an approximately 100-fold higher titer with Mnn2 mannan compared to wild type mannan suggests that branching actually blocks binding of the antibody to the α-1,6 backbone. Finally, there was complete congruence between presence of a Mnn9p homologue as determined by bioinformatics search (Table 4) and production of mannans in cell extracts that are reactive with mAb 2DA6 (FIG. 6).

Our survey of extracts from 16 fungi (FIG. 6) and six purified mannans (FIGS. 1 and 4) showed considerable variability in the sensitivity of mAb 2DA6 to detect them, i.e., mAb 2DA6 assay limit of detection. One possible explanation for differences in reactivity of mannans in fungal extracts is variability in either production or extractability of mannans. However, similar variability in reactivity of mAb 2DA6 with purified mannans suggests that structural differences likely explain differences in sensitivity. This argument is supported by a comparative evaluation of the reactivity of mAb 2DA6 with wild type and Mnn2 mannans (FIG. 4). Wild type mannan has extensive branching off the α-1,6 mannose backbone by α-1,2 residues; Mnn2 mannan lacks such branching and consists entirely of a long α-1,6-linked backbone. The limit of detection for the sandwich ELISA for Mnn2 mannan was >100 times lower than the limit of detection for wild type mannan. This result suggests that the α-1,2-linked mannose residues block mAb 2DA6 reactivity.

The extent to which side chain blockade of antibody binding to the α-1,6 mannose backbone impacts utility for immunoassay will depend on the individual fungus and on requirements for assay sensitivity. For example, extracts from *Rhizopus* and *Mucor* spp. and the dermatophytes produced very high titers in the sandwich ELISA (FIG. 6), indicating that any side chains present had negligible blocking activity. In other instances, e.g., mannans of *Fusarium* or *Candida*, titers with mAb 2DA6 were lower, indicating that side chain blockade of mAb binding likely impacts assay sensitivity with these fungi (FIGS. 1 and 6). Importantly, the requirements for assay sensitivity will likely need to be determined on a case-by-case basis. For example, the concentration of *C. albicans* in swabs of vaginal candidiasis may be high, in which case, a clinically useful immunoassay is quite possible despite partial blockade of access to the backbone.

An alternative approach to assay development for cases in which side chain blockade does present an issue for assay utility would be sample treatment to remove blocking side chains. Side chains on some fungal mannans are susceptible to hydrolysis at high pH. In a similar manner, treatment of sample extracts with glycolytic enzymes could be used to increase immunoassay sensitivity for fungal mannans that have considerable substitution by α-1,2-linked side chains on the α-1,6-linked mannose backbone.

A major strength of a pan-fungal immunoassay constructed from mAb 2DA6 is the ability to broadly determine the presence of fungal infection. A positive result would trigger an early anti-fungal intervention. A negative result would facilitate antifungal stewardship and spare individuals or the environment possible exposure to the side effects of many antifungal agents. Notably, immunoassays constructed from mAb 2DA6 are very sensitive to the zygomycetes and are adaptable to point-of-need use. A further strength to the immunoassay format is the threshold needed to produce a positive reaction. Alternative diagnostic approaches such as culture or PCR have the potential for false positive reactions due to contamination or saprophytic colonization by low numbers of fungi. Immunoassays for detection of bacteria typically require $10^3$ to $10^5$ bacteria to produce a positive reaction. As a consequence a positive result typically indicates a significant infection. A similar threshold for a mannan immunoassay would likely limit positive reactions to biologically significant fungal infections. The weakness of a pan-fungal immunoassay is the absence of genus or species information. In some instances where there are different fungi on a differential diagnosis, identification at the genus or species level might impact the choice of antifungal. That said, early recognition of fungal infection, regardless of genus or species, would enable empiric therapy pending results of culture.

The ability to use bioinformatics searches for Mnn9p homologues to predict whether a given fungus might produce a mannan that is reactive with mAb 2DA6 greatly facilitates development of new applications for the pan-fungal immunoassay. One example of the potential utility of this approach is provided by bat white-nose syndrome, which is caused by the ascomycete *Pseudogymnoascus destructans*, which is currently causing catastrophic declines in multiple species of bats in eastern North America (Blehert et al., (2009) *Science* 323:227, Lorch et al., (2011) *Nature* 480:376-378). A bioinformatics search for Mnn9p homologues in *P. destructans* found a protein (NCBI accession # XP_012740031.1) with a high degree of homology (1e-83) (Tables 4 and 8). This in silico analysis was followed by direct experimentation which showed that an extract from *P. destructans* culture was reactive in a sandwich ELISA constructed from mAb 2DA6 (FIG. 6). In a similar manner, investigators can use bioinformatics analysis to predict potential success for use of the pan-fungal epitope as a target for immunodetection of a broad spectrum of fungal infections that threaten human, animal, plant or biodiversity health, e.g., Tables 5-11.

Potential applications of an antibody that targets the pan-fungal α-1,6 mannose backbone are not limited to immunoassay platforms such as ELISA or LFIA. One further application is that of immunohistopathology. Histopathology in invasive fungal disease is currently based on special stains such as calcofluor white, Grocott-Gomori's methenamine silver and periodic acid Schiff, among others. Immunostaining using fluorescent or enzyme labels that targeted the cell wall could increase sensitivity. Moreover, increased definition of the cell wall by binding of an antibody that reacts with both zygomycetes and ascomycetes (such as mAb 2DA6) could improve the distinction of aseptate hyphae (zygomycetes) from septate hyphae (invasive ascomycetious fungi).

In summary, an epitope found on the α-1,6 mannose backbone of fungal mannans is a target for the construction of immunoassays that detect the presence of fungi of the *Zygomycota* and *Ascomycota* phyla. Fungi of the *Chytridiomycota* and *Basidiomycota* do not produce the reactive epitope. This epitope is recognized by the mAb 2DA6. Bioinformatics analysis for production of Mnn9p, which is necessary for backbone synthesis, can be used to predict production of a mannan that is reactive with mAb 2DA6. Finally, immunoassays in ELISA and LFIA formats can detect mannan in extracts from fungal cultures and tissues from plants with infection by fungi having Mnn9p homologs.

Patent Deposit

Hybridoma 2DA6 3B11 used to produce mAb 2DA6 was deposited with the American Type Culture Collection (ATCC, 10801 University Boulevard, Manassas, Va. 20110 USA) on Apr. 8, 2016 and given Accession No. PTA-123011. Access to this deposit will be available during the pendency of this application to persons determined by the Commissioner of Patents and Trademarks to be entitled thereto under 37 CFR 1.14 and 35 USC 122. The deposit was made under the provisions of the Budapest Treaty on the International Recognition of the Deposit of Microorganisms for the Purposes of Patent Procedure and the Regulations thereunder (Budapest Treaty). The 2DA6 3B11 hybridoma deposited with the ATCC was taken from the same deposit maintained by the University of Nevada, Reno since prior to the filing date of this application. The deposit will be maintained at the ATCC Depository, which is a public depository, for a period of 30 years, or five years after the most recent request, or for the enforceable life of the patent, whichever is longer, and will be replaced if it becomes nonviable during that period.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, with art-recognized alternatives and using no more than routine experimentation, are within the scope of the present application.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition comprising a monoclonal antibody that specifically binds the α-1,6 mannose backbone of fungal mannan, wherein the antibody comprises an amino acid sequence encoded by at least a light chain nucleic acid sequence comprising SEQ ID NO: 1 of mAb 2DA6 or at least a heavy chain nucleic acid sequence comprising SEQ ID NO: 2 of mAb 2DA6.

2. The composition of claim 1, wherein mAb 2DA6 is produced by a hybridoma having ATCC Accession No. PTA-123011.

3. A composition comprising an antibody that specifically binds the α-1,6 mannose backbone of fungal mannan, wherein the antibody is a single chain
   scFv clone 11C16 comprising an amino acid sequence encoded by a light chain nucleic acid sequence comprising SEQ ID NO: 5 and a heavy chain nucleic acid sequence comprising SEQ ID NO: 6.

4. A kit for determining whether a sample contains a fungus, the kit comprising: a monoclonal antibody or a scFv that specifically binds the α-1,6 mannose backbone of fungal mannan in said sample, wherein the monoclonal antibody comprises an amino acid sequence encoded by at least a light chain nucleic acid sequence comprising SEQ ID NO: 1 of mAb 2DA6 or at least a heavy chain nucleic acid sequence comprising SEQ ID NO: 2 of mAb 2DA6; and instructional materials for the use thereof.

5. The kit of claim 4, wherein the monoclonal antibody is mAb 2DA6, and the scFv
   scFv clone 11C16 comprising an amino acid sequence encoded by a light chain nucleic acid sequence comprising SEQ ID NO: 5 and a heavy chain nucleic acid sequence comprising SEQ ID NO: 6.

6. A method of making a monoclonal antibody that specifically binds the α-1,6 mannose backbone of fungal mannan, wherein the antibody comprises an amino acid sequence encoded by at least a light chain nucleic acid sequence comprising SEQ ID NO: 1 of mAb 2DA6 or at least a heavy chain nucleic acid sequence comprising SEQ ID NO: 2 of mAb 2DA6, the method comprising:
   immunizing a mammal with *Saccharomyces* Mnn2,
   isolating B cells that produce an antibody that specifically binds the α-1,6 mannose backbone of fungal mannan,
   fusing the B cells with a cancer cell to generate a hybridoma cell that produces an antibody that specifically binds the α-1,6 mannose backbone of fungal mannan.

7. A method of making a monoclonal antibody that specifically binds the α-1,6 mannose backbone of fungal mannan, wherein the antibody comprises an amino acid sequence encoded by at least a light chain nucleic acid sequence comprising SEQ ID NO: 1 of mAb 2DA6 or at least a heavy chain nucleic acid sequence comprising SEQ ID NO: 2 of mAb 2DA6, the method comprising:
   immunizing a mammal with a substance having an effective amount of α-1,6 mannose,
   isolating B cells that produce an antibody that specifically binds the α-1,6 mannose backbone of fungal mannan,
   fusing the B cells with a cancer cell to make a hybridoma cell that produces an antibody that specifically binds the α-1,6 mannose backbone of fungal mannan.

8. A method of making a monoclonal antibody that specifically binds the α-1,6 mannose backbone of fungal mannan, wherein the antibody comprises an amino acid sequence encoded by at least a light chain nucleic acid sequence comprising SEQ ID NO: 1 of mAb 2DA6 or at least a heavy chain nucleic acid sequence comprising SEQ ID NO: 2 of mAb 2DA6, the method comprising:
   immunizing a mammal with a fungus comprising an α-1,6 mannose backbone,
   isolating B cells that produce an antibody that specifically binds the α-1,6 mannose backbone of fungal mannan,
   fusing the B cells with a cancer cell to make a hybridoma cell that produces an antibody that specifically binds the α-1,6 mannose backbone of fungal mannan.

9. The method of claim 8, wherein the fungus comprising an α-1,6 mannose backbone is selected from the group consisting of *Aspergillus* spp., *Candida* spp., *Mucor* spp., *Rhizopus* spp., and *Fusarium* spp.

10. The method of claim 6, wherein the mammal that is immunized is a Diversity Outbred mouse.

* * * * *